United States Patent
Broedl et al.

(10) Patent No.: US 9,949,997 B2
(45) Date of Patent: Apr. 24, 2018

(54) PHARMACEUTICAL COMPOSITION, METHODS FOR TREATING AND USES THEREOF

(71) Applicant: Boehringer Ingelheim International GmbH, Ingelheim am Rhein (DE)

(72) Inventors: Uli Christian Broedl, Mainz am Rhein (DE); Odd-Erik Johansen, Hoevik (NO); Gabriel Woojai Kim, Mainz am Rhein (DE); Eric Williams Mayoux, Schemmerhofen (DE); Afshin Salsali, Princeton, NJ (US); Nima Soleymanlou, Maple (CA); Maximilian von Eynatten, Mainz (DE); Hans-Juergen Woerle, Munich (DE); David Z. I. Cherney, Toronto (CA); Bruce A. Perkins, Toronto (CA); Andreas Daiber, Scheessel (DE); Thomas Muenzel, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 44 days.

(21) Appl. No.: 14/918,713

(22) Filed: Oct. 21, 2015

(65) Prior Publication Data
US 2016/0038523 A1 Feb. 11, 2016

Related U.S. Application Data

(63) Continuation of application No. 14/244,196, filed on Apr. 3, 2014, now abandoned.

(60) Provisional application No. 61/942,301, filed on Feb. 20, 2014, provisional application No. 61/835,811, filed on Jun. 17, 2013, provisional application No. 61/835,809, filed on Jun. 17, 2013, provisional application No. 61/823,041, filed on May 14, 2013, provisional application No. 61/808,807, filed on Apr. 5, 2013.

(51) Int. Cl.
| | | |
|---|---|---|
| A61K 31/7048 | (2006.01) | |
| A61K 31/155 | (2006.01) | |
| A61K 31/522 | (2006.01) | |
| A61K 31/7034 | (2006.01) | |
| A61K 45/06 | (2006.01) | |
| A61K 9/20 | (2006.01) | |
| A61K 9/28 | (2006.01) | |

(52) U.S. Cl.
CPC ........ *A61K 31/7048* (2013.01); *A61K 9/2018* (2013.01); *A61K 9/2866* (2013.01); *A61K 31/155* (2013.01); *A61K 31/522* (2013.01); *A61K 31/7034* (2013.01); *A61K 45/06* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,145,684 A | 9/1992 | Liversidge et al. |
| 5,807,580 A | 9/1998 | Luber |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Cernea Simona. et al. "β-Cell Protection and Therapy for Latent Autoimmune Diabetes in Adults" Diabetes Care (2009) vol. 32, Supplement 2, pp. S246-S252.
Chen, L. H. et al. "Inhibition of the sodium glucose co-transporter-2: its beneficial action and potential combination therapy for type 2 diabetes mellitus" Diabetes, Obesity and Metabolism, (2013) vol. 15, pp. 392-402.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Nov. 14, 2012. 4 pgs.
Clinical Trials: NCT01167881. "Efficacy and Safety of Empagliflozin (BI 10773) With Metformin in Patients with Type 2 Diabetes" Sponsor: Boehringer Ingelheim Pharmaceuticals, Updated Date: Apr. 3, 2013, 4 pgs.

(Continued)

*Primary Examiner* — Traviss C McIntosh, III
(74) *Attorney, Agent, or Firm* — Marc A. Began; Edouard G. Lebel

(57) ABSTRACT

The present invention relates to certain SGLT-2 inhibitors for treating and/or preventing oxidative stress, for example in patients with type 1 or type 2 diabetes, as well as to the use of such SGLT-2 inhibitors in treatment and/or prevention of cardiovascular diseases in patients, for example type 1 or type 2 diabetes patients. The present invention further relates to certain SGLT-2 inhibitors for treating and/or preventing a metabolic disorder and preventing, reducing the risk of or delaying the occurrence of a cardiovascular event in patients, for example patients with type 1 or type 2 diabetes.

18 Claims, 23 Drawing Sheets

(56) References Cited

U.S. PATENT DOCUMENTS

| | | | |
|---|---|---|---|
| 7,371,732 B2 | 5/2008 | Eickelmann et al. | |
| 7,375,087 B2 | 5/2008 | Teranishi et al. | |
| 7,375,090 B2 | 5/2008 | Himmelsbach et al. | |
| 7,375,213 B2 | 5/2008 | Deshpande et al. | |
| 7,393,836 B2 | 7/2008 | Eckhardt et al. | |
| 7,407,955 B2 | 8/2008 | Himmelsbach et al. | |
| 7,417,032 B2 | 8/2008 | Eckhardt et al. | |
| 7,419,959 B2 | 9/2008 | Eckhardt et al. | |
| 7,541,341 B2 | 6/2009 | Fushimi et al. | |
| 7,579,449 B2 | 8/2009 | Eckhardt et al. | |
| 7,589,193 B2 | 9/2009 | Washburn et al. | |
| 7,662,790 B2 | 2/2010 | Himmelsbach et al. | |
| 7,674,486 B2 | 3/2010 | Bhaskaran et al. | |
| 7,683,160 B2 | 3/2010 | Eckhardt et al. | |
| 7,687,469 B2 | 3/2010 | Eckhardt et al. | |
| 7,713,938 B2 * | 5/2010 | Himmelsbach | C07H 15/00 514/23 |
| 7,723,309 B2 | 5/2010 | Himmelsbach et al. | |
| 7,723,379 B2 | 5/2010 | Romanczyk, Jr. et al. | |
| 7,745,414 B2 | 6/2010 | Eckhardt et al. | |
| 7,772,191 B2 | 8/2010 | Eckhardt et al. | |
| 7,772,192 B2 | 8/2010 | Esko | |
| 7,772,378 B2 | 8/2010 | Himmelsbach et al. | |
| 7,772,407 B2 | 8/2010 | Imamura et al. | |
| 7,776,830 B2 | 8/2010 | Eckhardt et al. | |
| 7,847,074 B2 | 12/2010 | Eckhardt et al. | |
| 7,851,502 B2 | 12/2010 | Bindra et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 8,119,648 B2 | 2/2012 | Himmelsbach et al. | |
| 8,178,541 B2 | 5/2012 | Himmelsbach et al. | |
| 8,232,281 B2 | 7/2012 | Dugi et al. | |
| 8,283,326 B2 | 10/2012 | Eckhardt et al. | |
| 8,507,450 B2 | 8/2013 | Eckhardt et al. | |
| 8,551,957 B2 * | 10/2013 | Dugi | A61K 31/70 514/23 |
| 8,557,782 B2 | 10/2013 | Eckhardt et al. | |
| 8,802,842 B2 | 8/2014 | Weber et al. | |
| 9,024,010 B2 | 5/2015 | Weber et al. | |
| 9,034,883 B2 | 5/2015 | Klein et al. | |
| 9,127,034 B2 | 9/2015 | Eckhardt et al. | |
| 9,192,616 B2 | 11/2015 | Johnson | |
| 2001/0018090 A1 | 8/2001 | Noda et al. | |
| 2002/0137903 A1 | 9/2002 | Ellsworth et al. | |
| 2002/0198205 A1 | 12/2002 | Himmelsbach et al. | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2003/0212070 A1 | 11/2003 | Schwink et al. | |
| 2004/0138148 A1 | 7/2004 | Fushimi et al. | |
| 2004/0138439 A1 | 7/2004 | Deshpande et al. | |
| 2004/0247677 A1 | 12/2004 | Oury et al. | |
| 2005/0065098 A1 | 3/2005 | Fujikura et al. | |
| 2005/0085680 A1 | 4/2005 | Auerbach et al. | |
| 2005/0124555 A1 | 6/2005 | Tomiyama et al. | |
| 2005/0187168 A1 | 8/2005 | Eickelmann et al. | |
| 2005/0209166 A1 | 9/2005 | Eckhardt et al. | |
| 2005/0233982 A1 | 10/2005 | Himmelsbach et al. | |
| 2005/0234108 A1 | 10/2005 | Himmelsbach et al. | |
| 2006/0009400 A1 | 1/2006 | Eckhardt et al. | |
| 2006/0019948 A1 | 1/2006 | Eckhardt et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2006/0074031 A1 | 4/2006 | Eckhardt et al. | |
| 2006/0079541 A1 | 4/2006 | Langkopf et al. | |
| 2006/0142210 A1 | 6/2006 | Eckhardt et al. | |
| 2006/0189548 A1 | 8/2006 | Himmelsbach et al. | |
| 2006/0210627 A1 | 9/2006 | Pfeffer et al. | |
| 2006/0234953 A1 | 10/2006 | Himmelsbach et al. | |
| 2006/0251728 A1 | 11/2006 | Himmelsbach et al. | |
| 2006/0258749 A1 | 11/2006 | Eckhardt et al. | |
| 2006/0287242 A1 | 12/2006 | Ewing et al. | |
| 2007/0004648 A1 | 1/2007 | Himmelsbach et al. | |
| 2007/0027092 A1 | 2/2007 | Himmelsbach et al. | |
| 2007/0042042 A1 | 2/2007 | Jo et al. | |
| 2007/0049537 A1 | 3/2007 | Eckhardt et al. | |
| 2007/0054867 A1 | 3/2007 | Eckhardt et al. | |
| 2007/0073046 A1 | 3/2007 | Eckhardt et al. | |
| 2007/0249544 A1 | 10/2007 | Himmelsbach et al. | |
| 2007/0259821 A1 | 11/2007 | Eckhardt et al. | |
| 2007/0281940 A1 | 12/2007 | Dugi et al. | |
| 2008/0058379 A1 | 3/2008 | Eckhardt et al. | |
| 2008/0107731 A1 | 5/2008 | Kohlrausch et al. | |
| 2008/0234367 A1 | 9/2008 | Washburn et al. | |
| 2008/0287529 A1 | 11/2008 | Deshpande et al. | |
| 2009/0023913 A1 | 1/2009 | Eckhardt et al. | |
| 2009/0137499 A1 * | 5/2009 | Honda | C07H 15/203 514/27 |
| 2009/0281078 A1 | 11/2009 | Routledge et al. | |
| 2009/0318547 A1 | 12/2009 | Eckhardt et al. | |
| 2009/0326215 A1 | 12/2009 | Eckhardt et al. | |
| 2010/0069310 A1 | 3/2010 | Himmelsbach et al. | |
| 2010/0074950 A1 | 3/2010 | Sesha | |
| 2010/0081625 A1 | 4/2010 | Wienrich et al. | |
| 2010/0093654 A1 | 4/2010 | Himmelsbach et al. | |
| 2010/0099641 A1 | 4/2010 | Himmelsbach et al. | |
| 2010/0179191 A1 | 7/2010 | Himmelsbach et al. | |
| 2010/0209506 A1 | 8/2010 | Eisenreich | |
| 2010/0240879 A1 | 9/2010 | Eckhardt et al. | |
| 2010/0249392 A1 | 9/2010 | Eckhardt et al. | |
| 2010/0298243 A1 | 11/2010 | Manuchehri et al. | |
| 2010/0317847 A1 | 12/2010 | Eckhardt et al. | |
| 2011/0014284 A1 | 1/2011 | Eisenreich et al. | |
| 2011/0015225 A1 | 1/2011 | Murata et al. | |
| 2011/0046076 A1 | 2/2011 | Eickelmann et al. | |
| 2011/0046087 A1 | 2/2011 | Eickelmann et al. | |
| 2011/0065731 A1 | 3/2011 | Dugi et al. | |
| 2011/0077212 A1 | 3/2011 | Seed et al. | |
| 2011/0098240 A1 | 4/2011 | Dugi et al. | |
| 2011/0178033 A1 | 7/2011 | Eckhardt et al. | |
| 2011/0195917 A1 | 8/2011 | Dugi et al. | |
| 2011/0206766 A1 | 8/2011 | Friedl et al. | |
| 2011/0236477 A1 | 9/2011 | Schneider et al. | |
| 2011/0237526 A1 | 9/2011 | Weber et al. | |
| 2011/0237789 A1 | 9/2011 | Weber et al. | |
| 2012/0041069 A1 | 2/2012 | Sesha | |
| 2012/0071403 A1 | 3/2012 | Strumph et al. | |
| 2012/0094894 A1 | 4/2012 | Graefe-Mody et al. | |
| 2012/0121530 A1 | 5/2012 | Klein et al. | |
| 2012/0196812 A1 | 8/2012 | Eickelmann et al. | |
| 2012/0219622 A1 | 8/2012 | Kohlrausch et al. | |
| 2012/0283169 A1 | 11/2012 | Grempler et al. | |
| 2012/0296080 A1 | 11/2012 | Eckhardt et al. | |
| 2013/0035281 A1 | 2/2013 | Klein et al. | |
| 2013/0035298 A1 | 2/2013 | Broedl et al. | |
| 2013/0064887 A1 | 3/2013 | Ito et al. | |
| 2013/0096076 A1 | 4/2013 | Dugi et al. | |
| 2013/0137646 A1 | 5/2013 | Wienrich et al. | |
| 2013/0236543 A1 | 9/2013 | Ito et al. | |
| 2013/0252908 A1 | 9/2013 | Mayoux et al. | |
| 2014/0031301 A1 | 1/2014 | Eickelmann et al. | |
| 2014/0038911 A1 | 2/2014 | Eickelmann et al. | |
| 2014/0046046 A1 | 2/2014 | Eckhardt et al. | |
| 2014/0087996 A1 | 3/2014 | Klein et al. | |
| 2014/0088027 A1 | 3/2014 | Grempler et al. | |
| 2014/0256624 A1 | 9/2014 | Grempler et al. | |
| 2014/0303097 A1 | 10/2014 | Broedl et al. | |
| 2014/0303098 A1 | 10/2014 | Broedl et al. | |
| 2014/0315832 A1 | 10/2014 | Broedl et al. | |
| 2015/0272977 A1 | 10/2015 | Reiche et al. | |
| 2015/0322053 A1 | 11/2015 | Eckhardt et al. | |
| 2016/0000816 A1 | 1/2016 | Broedl et al. | |
| 2016/0030385 A1 | 2/2016 | Manuchehri et al. | |
| 2016/0038523 A1 | 2/2016 | Broedl et al. | |
| 2016/0038524 A1 | 2/2016 | Broedl et al. | |
| 2016/0038525 A1 | 2/2016 | Broedl et al. | |
| 2016/0074415 A1 | 3/2016 | Wienrich et al. | |
| 2017/0020907 A1 | 1/2017 | Eickelmann et al. | |
| 2017/0095424 A1 | 4/2017 | Ito et al. | |
| 2017/0106009 A1 | 4/2017 | Mayoux | |

(56) References Cited

U.S. PATENT DOCUMENTS

| | | |
|---|---|---|
| 2017/0189437 A1 | 7/2017 | Manuchehri et al. |
| 2017/0266152 A1 | 9/2017 | Broedl et al. |
| 2017/0305952 A1 | 10/2017 | Klein et al. |
| 2017/0333465 A1 | 11/2017 | Broedl et al. |

FOREIGN PATENT DOCUMENTS

| | | |
|---|---|---|
| CA | 2402609 A1 | 9/2001 |
| CA | 2423568 A1 | 4/2002 |
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2586938 A1 | 5/2006 |
| CA | 2649922 A1 | 11/2007 |
| CA | 2651019 A1 | 11/2007 |
| CA | 2720450 A1 | 10/2009 |
| CN | 1930141 A | 3/2007 |
| CN | 101638423 A | 2/2010 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1803729 A1 | 7/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2006176443 A | 7/2006 |
| JP | 2008540373 A | 11/2008 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 2002064549 | 8/2002 |
| WO | 2002068420 A1 | 9/2002 |
| WO | 2002083066 A2 | 10/2002 |
| WO | 2003015769 | 2/2003 |
| WO | 2003020737 A1 | 3/2003 |
| WO | 2003031458 A1 | 4/2003 |
| WO | 2003064411 | 8/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005011592 A2 | 2/2005 |
| WO | 2005012318 A2 | 2/2005 |
| WO | 2005012326 A1 | 2/2005 |
| WO | 2005021566 A2 | 3/2005 |
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |
| WO | 2005092877 A1 | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006048427 A1 | 5/2006 |
| WO | 2006064033 A2 | 6/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007136116 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2009123194 A1 | 10/2009 |
| WO | 2010045656 A2 | 4/2010 |
| WO | 2010049678 A2 | 5/2010 |
| WO | 2010072776 A1 | 7/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |

(56) References Cited

FOREIGN PATENT DOCUMENTS

| WO | 2011039107 A1 | 4/2011 |
|---|---|---|
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012065993 A1 | 5/2012 |
| WO | 2012106303 A1 | 8/2012 |
| WO | 2012107476 A1 | 8/2012 |
| WO | 2012120040 A1 | 9/2012 |
| WO | 2012163990 A1 | 12/2012 |
| WO | 2013007557 A1 | 1/2013 |
| WO | 2013131967 A1 | 9/2013 |
| WO | 2013139777 A1 | 9/2013 |
| WO | 2014011926 A1 | 1/2014 |
| WO | 2014161918 A1 | 10/2014 |
| WO | 2014170383 A1 | 10/2014 |
| WO | 2016046150 A1 | 3/2016 |

OTHER PUBLICATIONS

EMBASE Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.

EMBASE database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.

Foote, Celine et al. "Effects of SGLT2 inhibitors on cardiovascular outcomes" (2012) Diabetes & Vascular Disease Research, vol. 9, (2) pp. 117-123.

International Search Report for PCT/EP2014/056655 filed Apr. 3, 2014.

Kautz, S. et al. "Early insulin therapy prevents beta cell loss in a mouse model for permanent neonatal diabetes (Munich Ins2C95s)" Diabetologia (2012) vol. 55, pp. 382-391.

Non-Final Office Action dated Mar. 10, 2017 from U.S. Appl. No. 14/855,576, filed Sep. 16, 2015.

Osorio, Horacio et al. "Sodium-Glucose Cotransporter Inhibition Prevents Oxidative Stress in the Kidney of Diabetic Rats" (2012) Oxidative Medicine and Cellular Longevity, vol. 2012, Article ID 542042, 7 pgs.

Response dated Jun. 15, 2017 to Non-Final Office Action dated Mar. 10, 2017 from U.S. Appl. No. 14/855,576, filed Sep. 16, 2015.

Suzuki, Masayuki et al. "Tofogliflozin, a Potent and Hightly Specific Sodium/Glucose Cotransporter 2 Inhibitor, Improves Glycemic Control in Diabetic Rats and Mice" The Journal of Pharmacology and Experimental Therapeuticals, vol. 341, No. 3 pp. 692-701.

Vallon, Volker et al. "Knockout of Na-glucose transporter SGLT2 attenuates hyperglycemia and glomerular hyperfiltration but not kidney growth or injury in diabetes mellitus" (2012) Am J Physiol Renal Physiol, vol. 304, F156-F167.

Zhang, Wenbin et al. "EGT1442, a potent and selective SGLT2 inhibitor, attenuates blood glucose and HbA1c levels in db/db mice an prolongs the survival of stroke-prone rats" (2011) Pharmacological Research, vol. 63, pp. 284-293.

Abstract ASNO9L1_307a "Contact View (TH-P0751) Kidney Function and Response to Diabetes in Mice Lacking SGLT2", Vallon, Volker et al, Oct. 29, 2009, 1 pg.

Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.

Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.

Aires, Ines et al. "BI-10773, a sodium-glucose cotransporter 2 inhibitor for the potential oral treatment of type 2 diabetes mellitus" (2010) Current Opinion in Investigational Drugs, vol. 11 (10), pp. 1182-1190.

American Diabetes Association "Consensus Development Conference on Antipyschotic Drugs and Obesity and Diabetes" (2004) Diabetes Care, vol. 27, No. 2, pp. 596-601.

American Diabetes Association "Diagnosis and Classification of Diabetes Mellitus" Diabetes Care, vol. 33, Supplement 1, Jan. 2010. pp. S62-S69.

Anonymous "Efficacy and Safety of Empagliflozin (BI 10773) in Patients with Type 2 Diabetes and Renal Impairment" Jan. 3, 2013, XP055120166, www.clinicaltrials.gov/ct2/show/study/NCT01164501?term=empagliflozin&rank=26.

Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.

Anonymous, "Composition with a High Drug Load of Empagliflozin" Feb. 26, 2016, 3 pgs.

Ashiya, Mona et al. "Non-insulin therapies for type 2 diabetes" (2007) Nature Reviews, Drug Discovery vol. 6, 777-778.

Aulton, Michael E. "Pharmaceutics, The Science of Dosage Form Design" (2002) 2nd Edition, 404-409.

Bailey, Clifford J. "Renal Glucose Reabsorption Inhibitors to Treat Diabetes" (2011) Trends in Pharmacological Sciences, vol. 32, No. 2, 63-71.

Banker, Gilbert S. et al. "Modern Pharmaceutics, Third Edition, Revised and Expanded" (1996) Marcel Dekker, p. 596.

Baptista, Irina et al. "Pharmacological Management of Atypical Antipsychotic-Induced Weight Gain" (2008) CNS Drugs, 22, 6, pp. 478-495.

Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.

Baron, Kyle T. et al. "Population Pharmacokinetics and Exposure-Response (Efficacy and Safety/Tolerability) of Empagliflozin in Patients with Type 2 Diabetes" (2016) Diabetes Ther, 7: 455-471.

Bauer, Kurt H. et al. "Pharmazeutische Technologie" (1993) p. 293.

Bloomgarden, Zachary T. "Diabetes Treatment" Diabetes Care, (Mar. 2009) vol. 32, No. 3 pp. e25-30.

Boyda, Heidi N et al. "Preclinical models of antipsychotic drug-induced metabolic side effects" (2010) Trends in Pharmacological Sciences vol. 31, pp. 484-497.

Byrn, Stephen et al. "Pharmaceutical Solids: A Strategic Approach to Regulatory Considerations" Pharmaceutical Research, vol. 12, No. 7, (1995) pp. 945-954.

Campbell, R. Keith "Rationale for Dipeptidyl Peptidase 4 Inhibitors: A New Class of Oral Agents for the Treatment of Type 2 Diabetes Mellitus" (2007) The Annals of Pharmacotherapy, vol. 41, 51-60.

Cetrone, Michela et al. "Effects of the antidiabetic drugs on the age-related atrophy and sarcopenia associated with diabetes type II" Current Diabetes Reviews (2014) vol. 10, No. 4, pp. 231-237.

Cherney, David et al. "The effect of sodium glucose cotransporter 2 inhibition with empagliflozin on microalbuminuria and macroalbuminuria in patients with type 2 diabetes" (2016) Diabetologia, 11pgs.

Cherney, David Z.I. et al. "Pooled analysis of Phase III trials indicate contrasting influences of renal function on blood pressure, body weight, and HbA1c reductions with empagliflozin" (2017) Kidney International, 1-14.

Cherney, David Z.I. et al. "Renal Hemodynamic Effect of Sodium-Glucose Cotransporter 2 Inhibition in Patients with Type 1 Diabetes Mellitus" Circulation, (2014) V 129, pp. 587-597.

Chow, Francis CC, et al. "Challenges in achieving optimal glycemic control in type 2 diabetes patients with declining renal function: The Southeast Asia perspective" Journal of Diabetes Investigation, (2012) vol. 3, Issue 6, pp. 481-489.

Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.

(56) References Cited

OTHER PUBLICATIONS

Clinical Trials: NCT01011868 "Efficacy and Safety of BI 10773 in Combination with Insulin in Patients with Type 2 Diabetes" Sponsor: Boehringer Ingelheim Pharmaceuticals, Oct. 18, 2010, 3 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Jul. 15, 2010, 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Mar. 7, 2012, 3 pgs.
Deacon, Carolyn F. "Perspectives in Diabetes Therapeutic Strategies Based on Glucagon-Like Peptide 1" Diabetes, (2004) vol. 53 pp. 2181-2189.
Defronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.
Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.
Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.
Drug Watch "Type 2 Diabetes Mellitus" Formulary vol. 43 Aug. 2008 p. 304.
Drugbank. Mettormin. Accession No. DB00331 (APRD01099) https://www.drugbank.ca/drugs/DB00331. Drug created on Jun. 13, 2005/Updated on May 9, 2017.
Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.
Ettmayer, Peter et al. "Lessons Learned from Marketed and Investigational Prodrugs" (2004) Journal of Medicinal Chemistry, vol. 47, No. 10, pp. 2393-2404.
European Patent Application 14715578.2, EP2981271; "Third party observations pursuant to article 115 EPC" (2017) 28 pgs.
Farxiga, Prescribing Information, Reference ID 3433133, Manufactured by Bristol-Myers Squibb Company, published by the FDA on Jan. 8, 2014, 43 pgs.
Ferrannini, E. et al. "A Phase IIb, randomized, placebo-controlled study of the SGLT2 inhibitor empagliflozin in patients with type 2 diabetes" (2013) Diabetes, Obesity and Metabolism, 15: 721-728.
Ferrannini, Ele et al. "CV Protection in the EMPA-REG Outcome Trial: A "Thrifty Substrate" Hypothesis" Diabetes Care, Jun. 11, 2016, pp. 1-7.
Ferrannini, Ele et al. "Renal Glucose Handling: Impact of Chronic Kidney Disease (CKD) and SGLT2 Inhibition in Patients with Type 2 Diabetes" (2012) Clinical Diabetes/Therapeutics Posters, 1028-P, A264.
Fiese, Eugene F et al. "Preformulation" (1987) The Theory and Practice of Industrial Pharmacy, 28 pgs.
Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.
Gennaro, Alfonso R. "Remington: The Science and Practice of Pharmacy" Twentieth Edition (2000) 4 pgs.
Golay A. et al. "Link Between Obesity and Type 2 Diabetes" (2005) Best Practice & Research Clinical Endocrinology & Metabolism, vol. 19, No. 4, 649-663.

Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Harris, Maureen I. "Classification, Diagnostic Criteria, and Screening for Diabetes" (1995) Diabetes in America, 2nd Edition, pp. 15-36.
Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Heise, Tim et al. "Treatment with BI 1356, a Novel and Potent DPP-IV Inhibitor Significantly Reduces Glucose Excursions after an oGTT in Patients with Type 2 Diabetes" (2007) Diabetes, Supp 1, vol. 56, 4 pgs.
Henderson, David C. et al. "Clozapine and Hypertension: A Chart Review of 82 Patients" (2004) J Clin Psychiatry, 65, pp. 686-689.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Idris, Iskandar et al "Sodium-glucose co-transporter-2 inhibitors: an emerging new class of oral antidiabetic drug" (2009) Diabetes, Obesity and Metabolism, 11, 79-88.
International Search Report and Written Opinion for PCT/EP2012/062922 dated Aug. 14, 2012.
International Search Report for PCT/EP2011/054734 dated Aug. 12, 2011.
International Search Report for PCT/EP2011/069532 dated Dec. 15, 2011.
International Search Report for PCT/EP2012/052108 dated Mar. 8, 2012.
International Search Report for PCT/EP2012/060194 dated Jul. 17, 2012.
International Search Report for PCT/EP2013/055671 dated Apr. 16, 2013.
International Search Report for PCT/EP2014/056657 dated Apr. 3, 2014.
International Search Report for PCT/EP2014/057754 dated Apr. 16, 2014.
International Search Report for PCT/EP2014/057754 dated May 27, 2014.
International Search Report for PCT/EP2016/074601 dated Dec. 16, 2016.
Invokana, Prescribing Information, Manufactured by Janssen Ortho LLC., published by the FDA on Mar. 29, 2013, 41 pgs.
Isaji, Masayuki "Sodium-glucose cotransporter inhibitors for diabetes" Current Opinion in Investigational Drugs, (2007) vol. 8, No. 4, pp. 285-292.
Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.

(56) References Cited

OTHER PUBLICATIONS

Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.
Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Jones, Byrony "Empagliflozin—one step closer to glycaemic control in patients with type II diabetes and CXD?" (2014) Nature Reviews Nephrology 10, 181, 2 pgs.
Joshi, Shashank R. "Metformin: Old Wine in New Bottle—Evolving Technology and Therapy in Diabetes" Journal of Association of Physicians in India, (2005) vol. 53, pp. 963-972.
Kadowaki, T et al. "PPAR gamma agonist and antagonist" Nihon Yakurigaku Zasshi (2001) vol. 118, No. 9, pp. 321-326. (English abstract).
Kasichayanula, Sreeneeranj et al. "The Influence of Kidney Function on Dapagliflozin Exposure, Metabolism and Pharmacodynamics in Healthy Subjects and in Patients with Type 2 Diabetes Mellitus" (2012) British Journal of Clinical Pharmacology, vol. 76, Issue 3, pp. 432-444.
Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.
Kohan, Donald E. et al. "Abstract: [ITH-PO524] Efficacy and Safety of Dapagliflozin in Patients with Type 2 Diabetes and Moderate Renal Impairment" Nov. 10, 2011, Abstract Sessions, 1 pg, http://www.abstracts2view.com.
Kohan, Donald E. et al. "Long-term study of patients with type 2 diabetes and moderate renal impairment shows that dapagliflozin reduces weight and blood pressure but does not improve glycemic control" (2013) Kidney International; 85, 962-971.
Kojima, Naoki et al. "Effects of a New SGLT2 Inhibitor, Luseogliflozin on Diabetic Nephropathy in T2DN Rats" The Journal of Pharmacology and Experimental Therapeutics, (2013) V 345, pp. 464-472.
Lebovitz, Harold E. "Insulin secretagogues: old and new" (1999) Diabetes Review, vol. 7, 139-153.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Levetan, Claresa "Oral antidiabetic agents in type 2 diabetes" (2007) Current Medical Research and Opinion, vol. 23, No. 4, 945-952.
Lewin, Andrew et al "Initial Combination of Empagliflozin and Linagliptin in Subjects with Type 2 Diabetes" (2015) Diabetes Care, vol. 38, 394-402.
Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.
Li, Yazhou, et al."Glucagon-like Peptide-1 Receptor Signaling Modulates b Cell Apoptosis" (2003) The Journal of Biological Chemistry, vol. 278, No. 1, 471-478.
Liberman, Herbert A. et al. "Pharmaceutical Dosage Forms: Tablets, vol. 1" (1989) pp. 5-6.
Liberman, Joseph A. "Metabolic Changes Associated with Antipsychotic Use" Prim Care Companion J Clinc Psychiatry (2004) 6, pp. 8-13.
Lipworth, Brian J. "Clinical pharmacology of b3-adrenoceptors" Br J Clin Pharmacol (1996) pp. 291-300.
Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.

Macha, S. et al. "Pharmacokinetics, pharmacodynamics and safety of empagliflozin, a sodium glucose cotransporter 2 (SGLT2) inhibitor, in subjects with renal impairment" (2014) Diabetes, Obesity and Metabolism, 16: 215-222.
Magee, G.M. et al. "Is hyperfiltration associated with the future risk of developing diabetic nephropathy? A meta-analysis" Diabetologia (2009) 52: pp. 691-697.
Malatiali, Slava et al. "Phlorizin Prevents Glomerular Hyperfiltration but not Hypertrophy in Diabetic Rats" (2008) Experimental Diabetes Research, vol. 2008, 7 pgs.
Marchetti, Piero et al. "Pancreatic Islets from Type 2 Diabetic Patients Have Functional Defects and Increased Apoptosis that are Ameliorated by Metformin" The Journal of Clinical Endocrinology & Metabolism, (2004) vol. 89,(11) pp. 5535-5541.
Matsuyama, Tatsuo et al. "Glucagon-like peptide-1 (7-36 amide): a potent glucagonostatic and insulinotropic hormone" Diabetes Research and Clincial Practice (1988) 5, 281-284.
McMaster University, Chem2006 Lab Manual, 1997/98, Expt 1, Part B, pp. 1-9.
Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: May 26, 2010. 4 pgs.
Grempler, R et al. "Empagliflozin, a novel selective sodium glucose cotransporter-2 (SGLT-2) inhibitor: Characterisation and comparsion with other SGLT-2 inhibitors" Diabetes, Obesity and Metabolism, (2012) vol. 14, pp. 33-90.
Lancet "Getting to the heart of the matter in type 2 diabetes" Editorial, (2015) 1 pg.
Zinman, Bernard et al. "Empagliflozin, Cardiovascular Outcomes and Mortality in Type 2 Diabetes" (2015) The New England Journal of Medicine, 373:22 pp. 2117-2128.
Merck Manual Online Edition, "Diabetes Mellitus" http://www.merckmanuals.com/professional/endocrine_and metabolic_disorders/diabetes_mellitus_and disorders of carbohyrate_metabolism/diabetes_mellitus_dm.html#v987998. last revision Jun. 2008 by Preeti Kishore M.D.
Merriam-Webster's Collegiate Dictionary,definition of prevent, published 1998 by Merriam-Webster Inc. p. 924.
Miller, Del D. "Review and Management of Clozapine Side Effects" (2000) J Clinc Psychiatry, 61 (Suppl 8) pp. 14-17.
Miyagawa, Junichiro et al. "Combined use between incretin-related meidcations and other medications" (2010) Diagnosis and Treatment, vol. 98, No. 3, 423-436.
Mogensen, Carl Erik "Perspectives in Diabetes Prediction of Clinical Diabetic Nephropathy in IDDM Patients Alternatives to Microalbuminuria?" Diabetes (1990) vol. 39, pp. 761-767.
Mojsov, Svetlana "Insulinotropin: Glucagon-like Peptide I (7-37) Co-encoded in the Glucagon Gene is a Potent Stimulator of Insulin Release in the Perfused Rat Pancreas" J. Clin. Invest. (1987) vol. 79, 616-619.
Mooradian, Arsharg D. et al. "Narrative Review: A Rational Approach to Starting Insulin Therapy" (2006) Annals of Internal Medicine, vol. 145, pp. 125-134.
Nair, S. et al. "From history to reality: sodium glucose co-transporter 2 inhibitors—a novel therapy for type 2 diabetes mellitus" (2010) Pract Diab Int, vol. 27, No. 7, pp. 311-316.
Nathan, D.M. et al. "Medical management of hyperglycaemia in type 2 diabetes mellitus: a consensus algorithm for the initiation and adjustment of therapy" Diabetologia (2009) 52, 17-30.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Office Action dated Mar. 10, 2017, U.S. Appl. No. 14/918,713, filed Oct. 21, 2015, first named inventor Uli Christian Broedl.
Oku, Akira et al. "T-1095, an Inhibitor of Renal Na+—Glucose Cotransporters, May Provide a Novel Approach to Treating Diabetes" (1999) Diabetes, vol. 48, 1794-1800.

(56) References Cited

OTHER PUBLICATIONS

Oku, Akira., et al; T-1095, An Inhibitor or renal Na+—Glucose Cotransporters, May Provide a Novel Approach to Treating Diabetes; Diabetes (1999) vol. 48 pp. 1794-1800.
Panchapakesan, Usha et al. Effects of SGLT2 Inhibition in Human Kidney Proximal Tubular Cells—Renoprotection in Diabetic Nephropathy? PLOS one, (2013) vol. 8, Issue 2, e54442, 8 pgs.
Patane, Giovanni et al. "Mefformin Restores Insulin Secretion Altered by Chronic Exposure to Free Fatty Acids or High Glucose, A Direct Mefformin Effect on Pancreatic b-Cells" (2000) Diabetes, vol. 49, pp. 735-740.
Patil, Basanagouda M. et al. "Elevation of systolic blood pressure in an animal model of olanzapine induced weight gain" (2006) European Journal of Pharmacology, vol. 551, pp. 112-115.
Perkins, Bruce A. et al. "Sodium-Glucose Cotransporter 2 Inhibition and Glycemic Control in Type 1 Diabetes: Results of an 8-Week Open-Label Proof-of-Concept Trial" (2014) Diabetes Care, vol. 37, pp. 1480-1483.
Pham, David et al. "Impact of empagliflozin in patients with diabetes and heart failure" (2017) Trends in Cardiovascular Medicine, vol. 27, pp. 144-151.
Piya, Milan K. et al. "Emerging treatment options for type 2 diabetes" British Journal of Clinical Pharmacology, (2010) vol. 70, No. 5, pp. 631-644.
Poole, Chris D. et al. "The prescription cost of managing people with type 1 and type 2 diabetes following initiation of treatment with either insulin glargine or insulin detemir in routine general practice in the UK: a retrospective database analysis" (2007) Current Medical Research and Opinion, vol. 23, S. 1, pp. S41-S48.
Powers, Richard E. et al. "Understanding the Side Effects of Neuroleptics" (2008) Bureau of Geriatric Psychiatry/DETA, pp. 17-24.
Pratley, Richard E. et al. "Inhibition of DPP-4: a new therapeutic approach for the treatment of type 2 diabetes" (2007) Current Medical Research and Opinion, vol. 23, No. 4, 919-931.
Printz, Richard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Pschyrembel et al. Clinical Dictionary, 257th Edition, Diabetes Mellitus, (1993) 320-321.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Richardson, H. et al. "Effects of rosiglitazone and metformin on pancreatic beta cell and gene expression" (2006) Diabetologia V 49, pp. 685-696.
Rieusset, Jennifer et al. "Insulin Acutely Regulates the Expression of the Peroxisome Proliferator-Activated Receptor—y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.
Rosenstock, J. et al. "Efficacy and safety of empagliflozin, a sodium glucose cotransporter (SGLT2) inhibitor, as add-on to metformin in type 2 diabetes with mild hyperglycaemia" (2013) Diabetes, Obesity and Metabolism, 15: 1154-1160.
Rosenstock, J. et al. "Impact of empagliflozin added on to basal insulin in type 2 diabetes inadequately controlled on basal insulin: a 78-week randomized, double-blind, placebo-controlled trial" (2015) Diabetes, Obesity and Metabolism, 17: 936-948.
Rosenstock, Julio et al. "Improved Glucose Control with Weight Loss, Lower Insulin Doses, and No Increased Hypoglycemia with Empagliflozin Added to Titrated Multiple Daily Injections of Insulin in Obese Inadequately Controlled Type 2 Diabetes" (2014) Diabetes Care, vol. 37, pp. 1815-1823.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 613-615.
Shannon, James A. et al. "The Excretion of Inulin, Xylose and Urea by Normal and Phlorizinized Man" New York University College of Medicine, Department of Physiology, Feb. 13, 1935, 393-401.
Sherwin, Robert S. et al. "The Prevention or Delay of Type 2 Diabetes" Diabetes Care, (2002) vol. 25, No. 4, pp. 742-749.
Singhal, Dharmendra et al. "Drug polymorphism and dosage form design: a practical perspective" Advanced Drug Delivery Reviews, 56, (2004) pp. 335-347.
Skrtic, Marko et al. "Characterisation of glomerular haemodynamic responses to SGLT2 inhibition in patients with type 1 diabetes and renal hyperfiltration" (2014) Diabetolgia, 4 pgs.
Softeland, Eirik et al. "Empagliflozin as Add-on Therapy in Patients with Type 2 Diabetes Inadequately Controlled With Linagliptin and Metformin: A 24-Week Randomized, Double-Blind, Parallel-Group Trial" (2016) Diabetes Care, DOI:10.2337/dc16-1347, pp. 1-9.
Stella, Valentino J. "Prodrugs as therapeutics" (2004) Ashley Publications, vol. 14, No. 3, pp. 277-280.
Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) Liver International, vol. 31, 9, pp. 1285-1297.
Swarbrick et al., Encyclopedia of Pharmaceutical Technology, 2nd Edition, (2002) 4 pgs.
Tanaka, Chikako "Therapeutic Drugs for Metabolic Diseases, Chapter 2" (2002) New Yakurigaku (New Pharmacology) pp. 524-527.
Testa, Bernard "Prodrug research: futile or fertile?" (2004) Biochemical Pharmacology vol. 68, pp. 2097-2106.
Thomas, L., "Chronic treatment with the Dipeptidyl Peptidase-4 Inhibitor BI 1356[9R]-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, 556-563.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Thomson, Scott C. et al. "Acute and chronic effects of SGLT2 blockade on glomerular and tubular function in the early diabetic rat" (2012) Am J Physiol Regul Integr Comp Physiol, 302, R75-R83.
Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.
Threlfall, Terry "Structural and Thermodynamic Explanations of Ostwald's Rule" Organic Process Research & Development (2003) vol. 7, pp. 1017-1027.
Tsujihara, Kenji et al. "Na+—Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.
Ueta, Kiichiro., et al; Long-Term Treatment with the Na+—Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
United States Pharmacopoeia, The National Formulary, (2005) USP 28, NF 23, p. 2711.

(56) References Cited

OTHER PUBLICATIONS

Unknown "Intensification of Development of SGLT inhibitor—New Alternative of Antidiabetic" Aug. 21, 2007; 2 pgs; http://www.yakuji.co.jp/entry4100.html.
Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.
Veltkamp, Stephan A. et al. "[1127-P] The Effect of Renal Impairment on the Pharmacokinetics and Urinary Glucose Excretion of the SGLT2 Inhibitor ASP1941 in Type 2 Diabetes Mellitus Patients" Clinical Therapeutics/New Technology, A309-A310.
Vervoort, G. et al. "Glomerular hyperfiltration in type 1 diabetes mellitus results from primary changes in proximal tubular sodium handling without changes in volume expansion" (2005) European Journal of Clinical Investigation vol. 35, pp. 330-336.
Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.
Wanner, Christoph et al. "Empagliflozin and Clinical Outcomes in Patients with Type 2 Diabetes, Established Cardiovascular and Chronic Kidney Disease" (2017) Circulation, American Heart Association, 66 pgs.
Wanner, Christoph et al. "Empagliflozin and Progression of Kidney Disease in Type 2 Diabetes" (2016) The New England Journal of Medicine, 1-12.
Weber, Ann E. "Dipeptidyl Peptidase IV Inhibitors for the Treatment of Diabetes" (2004) J. Med. Chem., 47, 4135-4141.
Websters Third New International Dictionary, Editor: GOVE, definition of prevent; 1963, 2 pgs.
Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.
Wolff, Manfred E., et al., "Burger's Medicinal Chemistry and Drug Discovery, Fifth Edition, vol. 1, Principles and Practices", (1995) Wiley-Interscience Publication pp. 975-977.
Woo, Young Sup et al. "Blood pressure changes during clozapine or olanzapine treatment in Korean schizophrenic patients" (2009) The World Journal of Biological Psychiatry, vol. 10(4); pp. 420-425.
Wu, Ren-Rong et al. "Lifestyle Intervention and Metformin for Treatment of Antipsychotic-Induced Weight Gain, A Randomized Controlled Trial" Journal of American Medical Association (2008) V 299, pp. 185-193.
Yale, J.F. et al. "Efficacy and safety of canagliflozin in subjects with type 2 diabetes and chronic kidney disease" Diabetes, Obesity and Metabolism (2013) vol. 15, pp. 463-473.
Yale, Jean-Francois et al. "Canagliflozin, a Sodium Glucose Co-Transporter 2 Inhibitor, Improves Glycemia and is Well Tolerated in Type 2 Diabetes Mellitus Subjects with Moderate Renal Impairment" Jun. 8, 2012, Poster presented at the 72nd Scientific Session of the American Diabetes Association, 2 pgs.
Yamada, Yuichiro et al. "Clinic: Careful Progress in the Field and new Therapeutic Methods" Medical Online, (2007) vol. 220, No. 13, pp. 1219-1221.
Yamout, Hala et al. "Efficacy and Safety of Canagliflozin in Patients with Type 2 Diabetes and Stage 3 Nephropathy" (2014) Am J Nephrol, 40: 64-74.
Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.
Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
Zimmermann, Grant R et al. "Multi-target therapeutics: when the whole is greater than the sum of the parts" (2007) Drug Discovery Today, vol. 12, 34-42.
Zinman, Bernard et al. "Empagliflozin, Cardiovascular Outcomes, and Mortality in Type 2 Diabetes" (2015) The New England Journal of Medicine, vol. 373;22, pp. 2117-2128.
Fitchett, David et al. "Heart failure outcomes with empagliflozin in patients with type 2 diabetes at high cardiovascular risk: results of the EMPA-REG Outcome® trial" (2016) European Heart Journal vol. 37, pp. 1526-1534.
Fujii, Masakazu et al. "Oxidative Stress and Diabetic Vascular Diseases" (2009) Angiology Frontier, vol. 8, No. 1, pp. 47-54.
Kashihara, Naoki et al. "Renin-Angiotensin System" (2011) Angiotensin Research, vol. 8, No. 2, pp. 40(96)-46(102).
Maeda, Yasutaka et al. "Oxidative Stress" (2010) Nippon Rinsho, vol. 68, No. 5, 814-818.
Shioi, Atsushi "Vascular Calcification and Remodeling in Diabetes" (2010) The Journal of Japanese College of Angiology, vol. 50, No. 5, 561-567.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Mar. 7, 2012. 5 pgs.
Final Office Action dated Sep. 28, 2017. U.S. Appl. No. 14/855,576, filed Sep. 16, 2015. First Named Inventor: Uli Christian Broedl; 23 pgs.

\* cited by examiner

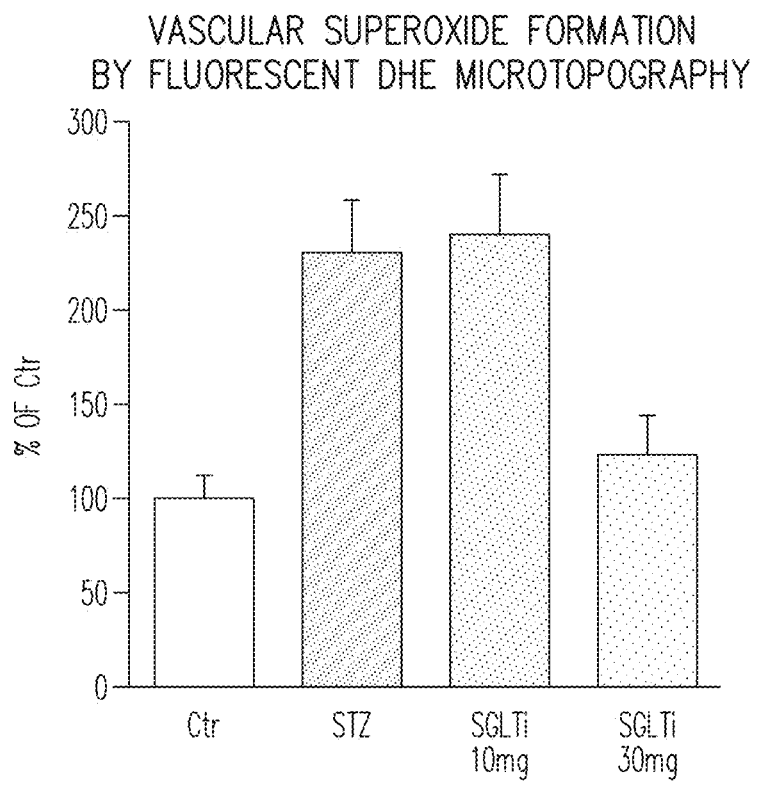
FIG. 12A
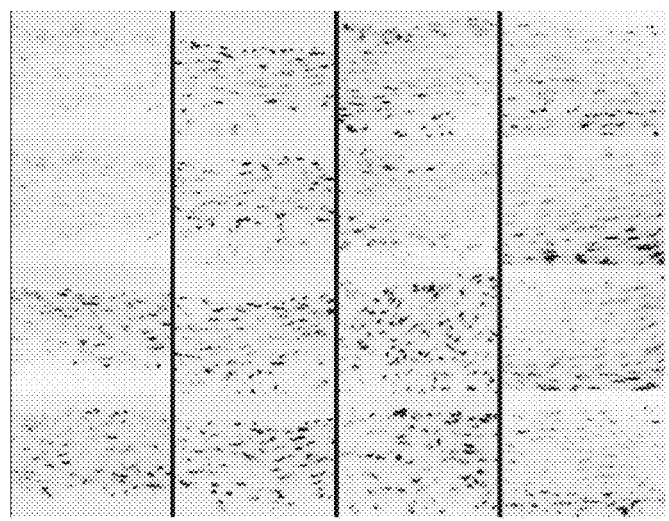

PHARMACEUTICAL COMPOSITION, METHODS FOR TREATING AND USES THEREOF

TECHNICAL FIELD OF THE INVENTION

The present invention relates to certain SGLT-2 inhibitors for treating and/or preventing oxidative stress, for example in patients with type 1 or type 2 diabetes mellitus, as well as to the use of such SGLT-2 inhibitors in treatment and/or prevention of cardiovascular diseases in patients, for example type 1 or type 2 diabetes mellitus patients. The present invention further relates to certain SGLT-2 inhibitors for treating and/or preventing a metabolic disorder and preventing, reducing the risk of or delaying the occurrence of a cardiovascular event in patients, for example patients with type 1 or type 2 diabetes mellitus.

BACKGROUND OF THE INVENTION

The rising prevalences of type 2 diabetes mellitus (T2DM) represent major challenges for global public health. Worldwide, there are more than 220 million patients with type 2 diabetes mellitus, figures which are projected to rise by 2030 (World Health Organisation 2010; International Diabetes Federation 2010). According to the US Centers for Disease Control and Prevention, rates of type 2 diabetes mellitus have tripled in the past 30 years. Diabetes now affects an estimated 23.6 million people in the United States; another 57 million have prediabetes. Prediabetes raises short-term absolute risk of type 2 diabetes mellitus five- to sixfold.

Type 2 diabetes mellitus is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes mellitus is associated with a two to five fold increase in cardiovascular disease risk.

After long duration of disease, most patients with type 2 diabetes mellitus will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c~0.9%). In addition, even in patients within the intensive treatment arm glycemic control deteriorated significantly over time and this was attributed to deterioration of β-cell function. Therefore many patients with type 2 diabetes mellitus remain inadequately treated, partly because of limitations in long term efficacy, tolerability and dosing inconvenience of existing antihyperglycemic therapies.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides, DPP-4 inhibitors and α-glucosidase inhibitors.

The high incidence of therapeutic failure is a major contributor to the high rate of long-term hyperglycemia-associated complications or chronic damages (including micro- and macrovascular complications such as e.g. diabetic nephropathy, retinopathy or neuropathy, or cardiovascular complications) in patients with type 2 diabetes mellitus.

Therefore, there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

SUMMARY OF THE INVENTION

The present invention relates to certain SGLT-2 inhibitors for treating and/or preventing oxidative stress, for example in patients with type 1 or type 2 diabetes mellitus. The present invention also relates to the use of such SGLT-2 inhibitors in the treatment and/or prevention of cardiovascular diseases in patients, for example in type 1 or type 2 diabetes mellitus patients. The present invention also relates to the use of such SGLT-2 inhibitors in treatment and/or prevention of a metabolic disorder in patients with or at risk of cardiovascular disease. The present invention further relates to certain SGLT-2 inhibitors for treating and/or preventing a metabolic disorder and preventing, reducing the risk of or delaying the occurrence of a cardiovascular event in patients, for example patients with type 1 or type 2 diabetes mellitus. The present invention also further relates to certain SGLT-2 inhibitors for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in patients having latent autoimmune diabetes in adults (LADA).

In one embodiment, the present invention provides a method for treating and/or preventing oxidative stress, vascular stress and/or endothelial dysfunction comprising administering empagliflozin, optionally in combination with one or more other therapeutic substances, to a patient in need thereof. In one embodiment, the patient is a non-diabetic patient or a patient with type 1 or type 2 diabetes mellitus. In one embodiment, the method is for treating and/or preventing endothelial dysfunction in a patient with type 1 or type 2 diabetes mellitus.

In one embodiment, the present invention provides a method for treating and/or preventing collagen deposition and/or vessel wall thickening comprising administering empagliflozin, optionally in combination with one or more other therapeutic substances, to a patient in need thereof. In one embodiment, the patient is a non-diabetic patient or a patient with type 1 or type 2 diabetes mellitus. In one embodiment, the method is for treating and/or preventing endothelial dysfunction in a patient with type 1 or type 2 diabetes mellitus.

In one embodiment, the present invention provides a method of treating type 2 diabetes mellitus in a patient with or at risk of oxidative stress, vascular stress and/or endothelial dysfunction, or diseases or conditions related or associated therewith, said method comprising administering empagliflozin, optionally in combination with one or more other therapeutic substances, to the patient.

In one embodiment, the present invention provides a method for using empagliflozin in one or more of the following methods:
  preventing, slowing the progression of, delaying or treating a metabolic disorder selected from the group consisting of type 1 or type 2 diabetes mellitus, impaired glucose tolerance, impaired fasting blood glucose, hyperglycemia, postprandial hyperglycemia, hyperinsulinemia and metabolic syndrome; or slowing the progression of, delaying or treating of pre-diabetes; or preventing, slowing the progression of, delaying or treating of an onset of type 2 diabetes mellitus; or improving glycemic control and/or for reducing of fasting plasma glucose, of postprandial plasma glucose and/or of glycosylated hemoglobin HbA1c; or preventing, slowing, delaying or reversing progression from impaired glucose tolerance, impaired fasting blood glucose, insulin resistance or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, dyslipidemia, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; or reducing body weight and/or body fat, or preventing an increase in body weight and/or body fat, or facilitating a reduction in body weight and/or body fat; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of ectopic fat, in particular liver fat; or for maintaining and/or improving the insulin sensitivity and/or for treating or preventing hyperinsulinemia and/or insulin resistance;

in a patient with or at risk of oxidative stress, vascular stress and/or endothelial dysfunction, or diseases or conditions related or associated therewith, or in a patient with or at risk of cardiovascular disease selected from myocardial infarction, stroke, peripheral arterial occlusive disease, or in a patient with one or more cardiovascular risk factors selected from A), B), C) and D):

A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease, B) advanced age >/=60-70 years, and C) one or more cardiovascular risk factors selected from
advanced type 1 or type 2 diabetes mellitus >10 years duration,
hypertension,
current daily cigarette smoking,
dyslipidemia,
obesity,
age >/=40
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative;

D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke,
peripheral occlusive arterial disease.

said method comprising administering empagliflozin, optionally in combination with one or more other therapeutic substances, to the patient.

In one embodiment, the method comprises treating type 1 or type 2 diabetes mellitus. In one embodiment, the patient is a type 1 or type 2 diabetes mellitus patient with or at risk of a cardiovascular disease selected from myocardial infarction, stroke, peripheral arterial occlusive disease.

In one embodiment, the patient is a patient with type 1 or type 2 diabetes mellitus or with pre-diabetes with one or more cardiovascular risk factors selected from A), B), C) and D):

A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease, B) advanced age >1=60-70 years, and C) one or more cardiovascular risk factors selected from
advanced type 1 or type 2 diabetes mellitus >10 years duration,
hypertension,
current daily cigarette smoking,
dyslipidemia,
obesity,
age >1=40,
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative;

D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke,
peripheral occlusive arterial disease.

In another embodiment, the present invention provides a method of preventing, reducing the risk of or delaying the occurrence of a cardiovascular event in a patient with type 1 or type 2 diabetes mellitus or with pre-diabetes, said method comprising administering empagliflozin, optionally in combination with one or more other therapeutic substances, to the patient. In one embodiment, the cardiovascular event is selected from cardiovascular death, non-fatal myocardial infarction, non-fatal stroke, hospitalisation for unstable angina pectoris and heart failure requiring hospitalisation. In one embodiment, the cardiovascular death is due to fatal myocardial infarction or fatal stroke. In one embodiment, the patient has or is at risk of a cardiovascular disease.

In one embodiment, the patient with type 1 or type 2 diabetes mellitus or with pre-diabetes has one or more cardiovascular risk factors selected from A), B), C) and D):

A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease,
B) advanced age >1=60-70 years, and
C) one or more cardiovascular risk factors selected from
advanced type 1 or 2 diabetes mellitus >10 years duration,
hypertension,
current daily cigarette smoking,
dyslipidemia,
obesity,
age >1=40
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative;
D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke,
peripheral occlusive arterial disease.

In one embodiment, the present invention provides a method of treating a metabolic disorder and preventing, reducing the risk of or delaying the occurrence of a cardiovascular event in a patient comprising administering empagliflozin, optionally in combination with one or more other therapeutic substances, to the patient. In one embodiment, the metabolic disorder is type 1 or 2 diabetes mellitus or pre-diabetes. In one embodiment, the cardiovascular event is selected from cardiovascular death, non-fatal myocardial infarction, non-fatal stroke, hospitalisation for unstable angina pectoris and heart failure requiring hospitalisation.

In one embodiment, the patient with type 1 or 2 diabetes mellitus or pre-diabetes has one or more cardiovascular risk factors selected from A), B), C) and D):
A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease,
B) advanced age >1=60-70 years, and
C) one or more cardiovascular risk factors selected from
advanced type 2 diabetes mellitus >10 years duration,
hypertension,
current daily cigarette smoking,
dyslipidemia,
obesity,
age >1=40,
metabolic syndrome, hyperinsulinemia or insulin resistance, and
hyperuricemia, erectile dysfunction, polycystic ovary syndrome, sleep apnea, or family history of vascular disease or cardiomyopathy in first-degree relative;
D) one or more of the following:
confirmed history of myocardial infarction,
unstable angina with documented multivessel coronary disease or positive stress test,
multivessel Percutaneous Coronary Intervention,
multivessel Coronary Artery By-pass Grafting (CABG),
history of ischemic or hemorrhagic stroke,
peripheral occlusive arterial disease.

In one embodiment, the present invention provides a method of treatment comprising:
a) identifying a patient in need of treatment for type 1 or type 2 diabetes and with or at risk of cardiovascular disease; and
b) administering empagliflozin to said patient.

In one embodiment, the present invention provides a method of treatment comprising:
a) selecting a patient with or at risk of cardiovascular disease from a population of patients in need of treatment for type 1 or type 2 diabetes mellitus;
b) selecting a type 1 or type 2 diabetes treatment that includes empagliflozin; and
c) administering empagliflozin to the patient selected in step a).

In one embodiment, the present invention provides a method of preventing, reducing the risk of or delaying the occurrence of a cardiovascular event in a patient diagnosed with type 1 or type 2 diabetes comprising:
a. determining the cardiovascular health of the patient;
b. identifying that the patient has or is at risk of a cardiovascular disease;
c. administering empagliflozin to the patient.

In one aspect, empagliflozin is administered to the patient if the patient has an elevated risk of a cardiovascular event.

In one embodiment, the patient has or is at risk of a cardiovascular disease selected from myocardial infarction, stroke, peripheral arterial occlusive disease.

In one embodiment, the present invention provides a method for treating a metabolic disorder in a patient comprising administering a pharmaceutical composition comprising empagliflozin to said patient, wherein the risk or occurrence of a cardiovascular event in said patient is reduced. In one embodiment, the cardiovascular event is selected from cardiovascular death, non-fatal myocardial infarction, non-fatal stroke, hospitalisation for unstable angina pectoris and heart failure requiring hospitalisation. In one embodiment, the risk or occurrence of a cardiovascular event is reduced when compared to a patient administered with a placebo on standard of care background medication. In one embodiment, the risk or occurrence of a cardiovascular event is reduced by 15% or more. In one embodiment, the risk or occurrence of a cardiovascular event is reduced by 16% or more, by 17% or more, by 18% or more, by 19% or more, by 20% or more, by 25% or more or by 30% or more. In one embodiment, pharmaceutical composition comprises 10 mg or 25 mg of empagliflozin. In one embodiment, the metabolic disorder is type 1 or type 2 diabetes mellitus or pre-diabetes.

In one embodiment, the patient is a patient with type 1 or type 2 diabetes or pre-diabetes with one or more cardiovascular risk factors selected from A), B), C) and D):
A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease,
B) advanced age >1=60-70 years, and
C) one or more cardiovascular risk factors selected from
advanced type 1 or type 2 diabetes mellitus >10 years duration,
hypertension,
current daily cigarette smoking,
dyslipidemia,
obesity,
age >1=40,
metabolic syndrome, hyperinsulinemia or insulin resistance, and hyperuricemia, erectile dysfunction, polycystic ovary syndrome, sleep apnea, or family history of vascular disease or cardiomyopathy in first-degree relative;
D) one or more of the following:
  confirmed history of myocardial infarction,
  unstable angina with documented multivessel coronary disease or positive stress test,
  multivessel Percutaneous Coronary Intervention,
  multivessel Coronary Artery By-pass Grafting (CABG),
  history of ischemic or hemorrhagic stroke,
  peripheral occlusive arterial disease.

In one embodiment, the hazard ratio at a one-sided α-level of 0.025 is <1.3.

In one embodiment, the present invention provides a method for reducing arterial stiffness in a patient comprising administering empagliflozin to the patient. In one aspect, the patient is a patient according to the present invention, in particular a patient with type 1 or type 2 diabetes or pre-diabetes.

In one aspect of the present invention, the one or more other therapeutic substances are selected from other antidiabetic substances, active substances that lower the blood sugar level, active substances that lower the total cholesterol, LDL-cholesterol, Non-HDL-cholesterol and/or Lp(a) level in the blood, active substances that raise the HDL-cholesterol level in the blood, active substances that lower blood pressure, active substances that are indicated in the treatment of atherosclerosis or obesity, antiplatelet agents, anticoagulant agents, and vascular endothelial protective agents. In one embodiment, the other antidiabetic substances are selected from metformin, sulphonylureas, nateglinide, repaglinide, PPAR-gamma agonists, alpha-glucosidase inhibitors, insulin and insulin analogues, GLP-1 and GLP-1 analogues and DPP-4 inhibitors. In one embodiment, the active substances that lower blood pressure are selected from angiotensin receptor blockers (ARB), angiotensin-converting enzyme (ACE) inhibitors, beta-blockers and diuretics. In one aspect, the present invention comprises administering empagliflozin in combination with one or more other antidiabetic substances selected from metformin, a sulphonylurea, nateglinide, repaglinide, a DPP-4 inhibitor, a PPAR-gamma agonist, an alpha-glucosidase inhibitor, insulin or insulin analogue, and GLP-1 or GLP-1 analogue. In one aspect, the present invention comprises administering empagliflozin in combination with metformin. In one aspect, the present invention comprises administering empagliflozin in combination with linagliptin. In one aspect, the present invention comprises administering empagliflozin in combination with metformin and linagliptin. In one aspect, empagliflozin is administered orally in a total daily amount of 10 mg or 25 mg.

In one embodiment, the present invention provides a method of treatment comprising:
  a) identifying a patient with type 1 or type 2 diabetes treated with a medication to treat a cardiovascular disease;
  b) administering empagliflozin to said patient; and
  c) reducing the dosage or regimen of said medication to treat a cardiovascular disease in said patient, while continuing to administer empagliflozin to said patient.

In one embodiment, the method further comprises monitoring the cardiac health of said patient.

In one embodiment, the present invention provides a method of treatment comprising:
  a. identifying a patient with type 1 or type 2 diabetes treated with a plurality of medications to treat a cardiovascular disease;
  b. administering empagliflozin to said patient; and
  c. reducing the number of medications to treat a cardiovascular disease in said patient, while continuing to administer empagliflozin to said patient.

In one embodiment, the method further comprises monitoring the cardiac health of said patient.

In one embodiment, the present invention provides a method of treatment comprising:
  a) determining the number, dosage and/or regimen of medications to treat a cardiovascular disease in a patient diagnosed with type 1 or type 2 diabetes;
  b) selecting empagliflozin as a treatment for type 2 diabetes for the patient; and
  c) administering empagliflozin to the patient while reducing the number and/or dosage of medications to treat a cardiovascular disease.

In one embodiment, the present invention provides a method of treatment comprising:
  a) administering empagliflozin to a patient diagnosed with type 1 or 2 diabetes;
  b) monitoring the cardiac health of said patient;
  c) adjusting the number, dosage and/or regimen of medications to treat a cardiovascular disease in said patient, while continuing to administer empagliflozin to the patient.

In one embodiment, the present invention provides a method of reducing the risk of a fatal or nonfatal cardiovascular event in a type 1 or type 2 diabetes patient comprising administering empagliflozin, optionally in combination with one or more other therapeutic substances, to the patient.

In one embodiment, the fatal or nonfatal cardiovascular event is stroke, myocardial infarction or heart failure. In one embodiment, the patient is at elevated risk of a cardiovascular event. In one embodiment the patient at elevated risk of a cardiovascular event has a history of coronary artery disease, peripheral arterial disease, stroke, transient ischemic attack or high-risk diabetes (insulin-dependent or non-insulin dependent) with evidence of end-organ damage. In one embodiment, the at least one of said one or more other therapeutic substances is a medication to treat a cardiovascular disease. In one embodiment, the one or more other therapeutic substances is a medication that lower blood pressure are selected from angiotensin receptor blockers (ARB), angiotensin-converting enzyme (ACE) inhibitors, and beta-blockers. In one embodiment, the one or more other therapeutic substances is a diuretic. In one embodiment, the number, dosage and/or regimen of said medications to treat a cardiovascular disease is reduced is said patient, while the administration of empagliflozin is continued.

In one embodiment, the present invention provides a method of reducing the risk of myocardial infarction, stroke or death from cardiovascular causes or heart failure, in particular heart failure requiring hospitalization, in a type 1 or type 2 diabetes patient comprising administering empagliflozin, optionally in combination with one or more other therapeutic substances, to the patient. In one embodiment, the patient is at elevated risk of a cardiovascular event. In one embodiment, the patient at elevated risk of a cardiovascular event has a history of coronary artery disease, peripheral arterial disease, stroke, transient ischemic attack or high-risk diabetes (insulin-dependent or non-insulin dependent) with evidence of end-organ damage. In one embodiment, at least one of said one or more other therapeutic substances is a medication to treat a cardiovascular disease. In one embodiment, the one or more other therapeutic substances is a medication that lower blood pressure are selected from angiotensin receptor blockers (ARB), angiotensin-converting enzyme (ACE) inhibitors, and beta-blockers. In one embodiment, the one or more other therapeutic substances is a diuretic. In one embodiment, the number, dosage and/or regimen of said medications to treat a cardiovascular disease is reduced is said patient, while the administration of empagliflozin is continued.

In a further embodiment, the present invention provides a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient having latent autoimmune diabetes in adults (LADA), the method comprising administering empagliflozin, optionally in combination with one or more other therapeutic substances, to the patient. In one embodiment, the patient having LADA is a patient in whom one or more autoantibodies selected from GAD (GAD-65, anti-GAD), ICA, IA-2A, ZnT8 (anti-ZnT8) and IAA are present.

In a further embodiment, the present invention provides a method for preserving pancreatic beta cells and/or their function in a patient having latent autoimmune diabetes in adults (LADA), the method comprising administering empagliflozin, optionally in combination with one or more other therapeutic substances, to the patient. In one embodiment, the patient having LADA is a patient in whom one or more autoantibodies selected from GAD (GAD-65, anti-GAD), ICA, IA-2A, ZnT8 (anti-ZnT8) and IAA are present.

In a further embodiment, the present invention provides a method for stimulating and/or protecting the functionality of pancreatic insulin secretion in a patient having latent autoimmune diabetes in adults (LADA), the method comprising administering empagliflozin, optionally in combination with one or more other therapeutic substances, to the patient. In one embodiment, the patient having LADA is a patient in whom one or more autoantibodies selected from GAD (GAD-65, anti-GAD), ICA, IA-2A, ZnT8 (anti-ZnT8) and IAA are present.

In a further embodiment, the present invention provides a method for treating and/or preventing LADA (latent autoimmune diabetes of adults), particularly in a patient having LADA in whom one or more autoantibodies selected from GAD (GAD-65, anti-GAD), ICA, IA-2A, ZnT8 (anti-ZnT8) and IAA are present, the method comprising administering empagliflozin, optionally in combination with one or more other therapeutic substances, to the patient.

In one aspect of the present invention, empagliflozin is administered orally, for example in a total daily amount of 10 mg or 25 mg. In one embodiment, empagliflozin is administered as a pharmaceutical composition comprising 10 mg or 25 mg of empagliflozin, for example as a tablet.

In one aspect of the present invention, in a method or use disclosed herein a patient is patient with type 2 diabetes (or type 2 diabetes patient), a patient treated for type 2 diabetes, a patient diagnosed with type 2 diabetes or a patient in need of treatment for type 2 diabetes. In one aspect, a patient is a patient with pre-diabetes.

The present invention further provides for empagliflozin or a pharmaceutical composition comprising empagliflozin for use as a medicament in any one of the methods described herein.

The present invention further provides for empagliflozin or a pharmaceutical composition comprising empagliflozin for use in the treatment of any one of the diseases or conditions described herein.

The present invention further provides for empagliflozin or a pharmaceutical composition comprising empagliflozin for use in the manufacture of a medicament for use in any one of the methods described herein.

Definitions

The term "active ingredient" of a pharmaceutical composition according to the present invention means the SGLT2 inhibitor according to the present invention. An "active ingredient is also sometimes referred to herein as an "active substance".

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The terms "obesity" or "being obese" and the like are defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio<1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28: 412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR}=[\text{fasting serum insulin }(\mu U/mL)]\times[\text{fasting plasma glucose(mmol/L)}/22.5]$$

Insulin resistance can be confirmed in these individuals by calculating the HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

"Pre-diabetes" is a general term that refers to an intermediate stage between normal glucose tolerance (NGT) and overt type 2 diabetes mellitus (T2DM), also referred to as intermediate hyperglycaemia. As such, it represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in the context of the present invention a patient being diagnosed of having "pre-diabetes" is an individual with diagnosed IGT or diagnosed IFG or diagnosed with both IGT and IFG. Following the definition according to the American Diabetes Association (ADA) and in the context of the present invention a patient being diagnosed of having "pre-diabetes" is an individual with:

a) a fasting plasma glucose (FPG) concentration<100 mg/dL [1 mg/dL=0.05555 mmol/L] and a 2-hour plasma glucose (PG) concentration, measured by a 75-g oral glucose tolerance test (OGTT), ranging between ≥140 mg/dL and <200 mg/dL (i.e., IGT); or b) a fasting plasma glucose (FPG) concentration between ≥100 mg/dL and <126 mg/dL and a 2-hour plasma glucose (PG) concentration, measured by a 75-g oral glucose tolerance test (OGTT) of <140 mg/dL (i.e., IFG); or c) a fasting plasma glucose (FPG) concentration between ≥100 mg/dL and <126 mg/dL and a 2-hour plasma glucose (PG) concentration, measured by a 75-g oral glucose tolerance test (OGTT), ranging between ≥140 mg/dL and <200 mg/dL (i.e., both IGT and IFG).

Patients with "pre-diabetes" are individuals being predisposed to the development of type 2 diabetes. Pre-diabetes extends the definition of IGT to include individuals with a fasting blood glucose within the high normal range≥100 mg/dL (J. B. Meigs, et al. Diabetes 2003; 52:1475-1484). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance:

An improvement of beta-cell function can be measured for example by determining a HOMA-index (homeostasis model assessment) for beta-cell function, HOMA-B, (Matthews et al., *Diabetologia* 1985, 28: 412-19), the ratio of intact proinsulin to insulin (Forst et al., *Diabetes* 2003, 52(Suppl. 1): A459), first and second phase insulin secretion after an oral glucose tolerance test or a meal tolerance test (Stumvoll et al., Diabetes care 2000, 23: 295-301), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "LADA" ("latent autoimmune diabetes of adults") refers to patients that have a clinical diagnosis of type 2 diabetes, but who are being detected to have autoimmunity towards the pancreatic beta cell. Latent autoimmune diabetes of adults (LADA) is also known as slowly progressive type 1 diabetes mellitus (T1 DM), "mild" T1 DM, non-insulin dependent type 1 DM, type 1½ DM, double diabetes or antibody positive type 2 DM (T2DM). LADA is often not clearly defined and, opposed to T1 DM, seldom or never presents with significant weight loss and ketoacidosis due to rapidly progressive β-cell failure.

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <7% or <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference>40 inches or 102 cm in men, and >35 inches or 94 cm in women; or with regard to a Japanese ethnicity or Japanese patients defined as waist circumference 85 cm in men and 90 cm in women;
2. Triglycerides: ≥150 mg/dL
3. HDL-cholesterol<40 mg/dL in men
4. Blood pressure≥130/85 mm Hg (SBP≥130 or DBP 85)
5. Fasting blood glucose≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "empagliflozin" refers to the SGLT2 inhibitor 1-chloro-4-(β-D-glucopyranos-1-yl)-2-[4-((S)-tetrahydrofuran-3-yloxy)-benzyl]-benzene of the formula

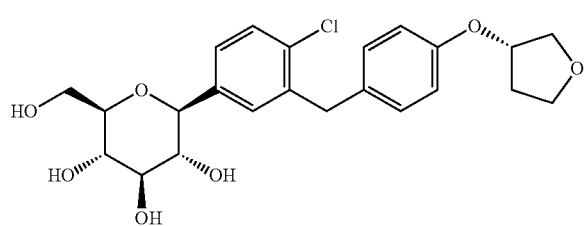 [SMILES: OC[C@H]1O[C@@H](c2ccc(Cl)c(Cc3ccc(O[C@H]4CCOC4)cc3)c2)[C@H](O)[C@@H](O)[C@@H]1O]

as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventively treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the before-mentioned types of tablets may be without or with one or more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

BRIEF DESCRIPTION OF THE DRAWINGS

FIGS. 12A and 12B: vascular superoxide formation by fluorescent DHE microtopography.

DETAILED DESCRIPTION OF THE INVENTION

Figures 1A, 1B, 1C:
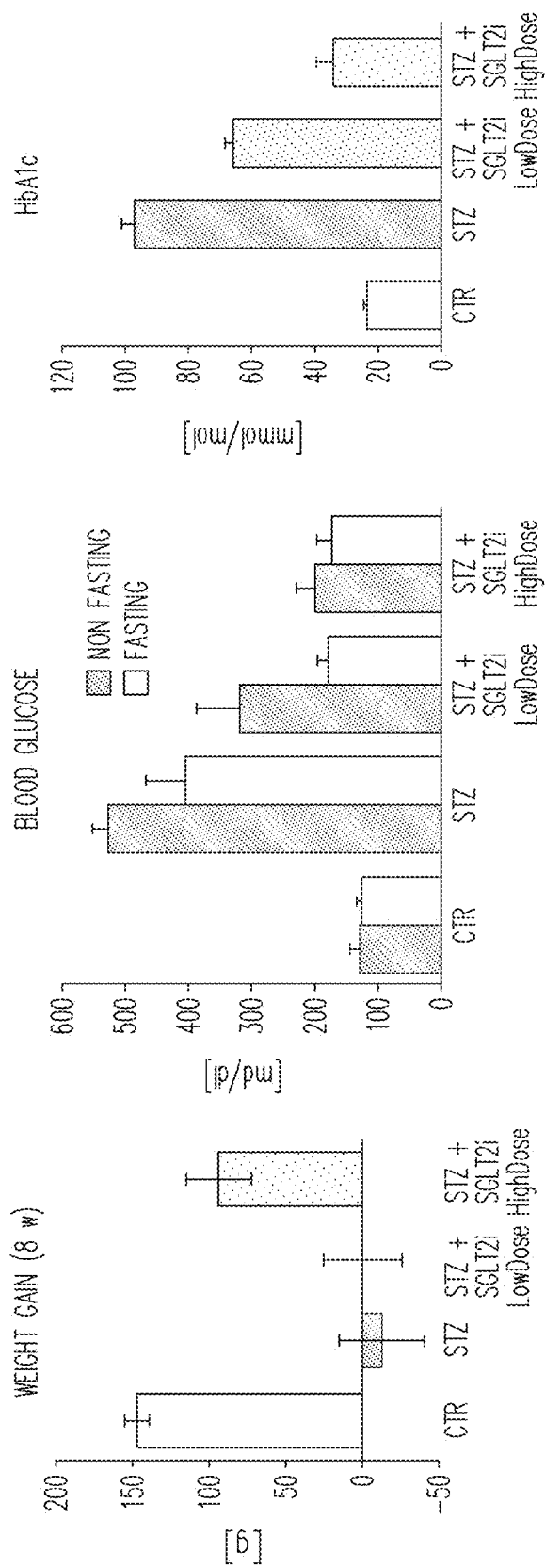
FIGS. 1A-C: weight gain, blood glucose (non-fasting and fasting, n=6-8) and HbA1c (n=5-6) in animals treated with empagliflozin.

The present invention relates to certain SGLT-2 inhibitors, in particular empagliflozin, for treating and/or preventing oxidative stress, for example in patients with type 1 or type 2 diabetes. The present invention further relates to certain SGLT-2 inhibitors, in particular empagliflozin, for treating and/or preventing endothelial dysfunction. The present invention further relates to certain SGLT-2 inhibitors, in particular empagliflozin, to reduce glucotoxicity and associated oxidative stress and inflammation in the tissues. The present invention also relates to the use of such SGLT-2 inhibitors in the treatment and/or prevention of cardiovascular diseases in patients, for example in type 1 or type 2 diabetes patients. The present invention also relates to the use of such SGLT-2 inhibitors, in particular empagliflozin, in treatment and/or prevention of metabolic disorders in patients with or at risk of cardiovascular disease. The present invention further relates to certain SGLT-2 inhibitors, in particular empagliflozin, for treating and/or preventing a metabolic disorder and preventing, reducing the risk of or delaying the occurrence of a cardiovascular event in patients, for example patients with type 1 or type 2 diabetes.

The present invention further relates to certain SGLT-2 inhibitors, in particular empagliflozin, for treating and/or preventing oxidative stress, vascular stress and/or endothelial dysfunction (e.g. in diabetes or non-diabetes patients), particularly independently from or beyond glycemic control.

The present invention further relates to certain SGLT-2 inhibitors, in particular empagliflozin, for treating and/or preventing collagen deposition and/or vessel wall thickening (e.g. in diabetes or non-diabetes patients), particularly independently from or beyond glycemic control.

The present invention further relates to certain SGLT-2 inhibitors, in particular empagliflozin, for treating and/or preventing hyperglycemia-induced or -associated oxidative stress (e.g. beyond glycemic control), as well as to the use of such SGLT-2 inhibitors in antidiabetic therapy.

The present invention further relates to certain SGLT-2 inhibitors, in particular empagliflozin, for treating and/or preventing metabolic disorders, such as diabetes, especially type 1 and type 2 diabetes mellitus and/or diseases related thereto (e.g. diabetic complications), particularly in patients having or being at risk of oxidative stress, vascular stress and/or endothelial dysfunction, or diseases or conditions related or associated therewith.

Further, the present invention relates to certain SGLT-2 inhibitors, in particular empagliflozin, for treating and/or preventing metabolic disorders, such as diabetes, especially type 1 and type 2 diabetes mellitus and/or diseases related thereto (e.g. diabetic complications), in patients having or being at risk of cardiovascular disease, such as e.g. myocardial infarction, stroke or peripheral arterial occlusive disease, or micro- or macroalbuminuria.

Further, the present invention relates to certain SGLT-2 inhibitors, in particular empagliflozin, for treating and/or preventing metabolic disorders, such as diabetes, especially type 1 and type 2 diabetes mellitus and/or diseases related thereto, in patients having or being at risk of micro- or macrovascular diabetic complications, such as e.g. diabetic retinopathy, diabetic neuropathy, diabetic nephropathy, or cardiovascular diseases (such as e.g. myocardial infarction, stroke or peripheral arterial occlusive disease).

Further, the present invention relates to certain SGLT-2 inhibitors, in particular empagliflozin, for modulating, blocking or reducing deleterious metabolic memory effect of (chronic or transient episodes of) hyperglycemia, particularly on diabetic complications.

Further, the present invention relates to certain SGLT-2 inhibitors, in particular empagliflozin, for treating, preventing or reducing risk for micro- or macrovascular diseases which may be induced, memorized by or associated with exposure to oxidative stress.

Furthermore, the present invention relates to a certain SGLT-2 inhibitor, in particular empagliflozin, for treating and/or preventing metabolic disorders, such as diabetes, especially type 1 and type 2 diabetes mellitus and/or diseases related thereto (e.g. diabetic complications), in patients with or at risk of cardiovascular disease, particularly in those type 1 or type 2 diabetes patients being at risk of cardiovascular events, such as type 1 or type 2 diabetes patients with one or more risk factors selected from previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I or II, e.g. left ventricular function<40%), or peripheral occlusive arterial disease), said method comprising administering a therapeutically effective amount of the SGLT-2 inhibitor, optionally in combination with one or more other therapeutic substances, to the patient.

Oxidative stress represents an imbalance between the production of reactive oxygen species (which include free radicals, which typically have an oxygen- or nitrogen based unpaired electron in their outer orbitals and peroxides) and a biological system's ability to readily detoxify the reactive intermediates or to repair the resulting damage. Disturbances in the normal redox state of tissues can cause toxic effects through the production of peroxides and free radicals that damage all components of the cell, including proteins, lipides and nucleic acid/DNA. Oxidative stress can target many organs (such as blood vessels, eyes, heart, skin, kidney, joints, lung, brain, immune system, liver, or multi-organs) and can be involved in many diseases and conditions. Examples of such diseases or conditions associated with oxidative stress include atherosclerosis (e.g. platelet activation and atheromatous plaque formation), endothelial dysfunction, restenosis, hypertension, peripheral occlusive vascular disease, ischemia-reperfusion injuries (e.g. renal, hepatic, cardiac or cerebral ischemia-reperfusion injuries), fibrosis (e.g. renal, hepatic, cardiac or pulmonary fibrosis); macular degeneration, retinal degeneration, cataracts, retinopathy; coronary heart disease, ischemia, myocardial infarction; psoriasis, dermatitis; chronic kidney disease, nephritis, acute renal failure, glomerulonephritis, nephropathy; rheumatoid arthritis, osteoarthritis; asthma, COPD, respiratory distress syndrome; stroke, neurodegenerative diseases (e.g. Alzheimer's disease, Parkinson's disease, Huntington's disease), schizophrenia, bipolar disorder, obsessive compulsive disorder; chronic systemic inflammations, perivascular inflammation, autoimmune disorders, multiple sclerosis, lupus erythematosus, inflammatory bowel disease, ulcerative colitis; NAFLD/NASH; chronic fatigue syndrome, polycystic ovary syndrome, sepsis, diabetes, metabolic syndrome, insulin resistance, hyperglycemia, hyperinsulinemia, dyslipidemia, hypercholesterolemia, hyperlipidemia, etc. In addition to their original pharmacological properties, certain drugs used clinically, including, without being limited, antihypertension agents, angiotensin receptor blockers and antihyperlipidemic agents such as statins, protect various organs via anti-oxidative stress mechanisms.

Patients with or at risk of oxidative and/or vascular stress can be diagnosed by determining patient's oxidative stress markers, such as e.g. oxidized LDL, markers of inflammatory status (e.g. pro-inflammatory interleukins), 8-OHdG, isoprostanes (e.g. F2-isoprostanes, 8-iso-prostaflandin F2alpha), nitrotyrosine, or N-carboxymethyl lysine (CML).

Endothelial dysfunction, commonly assessed clinically as impaired endothelium-dependent vasomotion (e.g. imbalance between vasodilating and vasoconstricting), is a physiological disability of endothelial cells, the cells that line the inner surface of blood vessels, arteries and veins, that prevents them from carrying out their normal biochemical functions. Normal endothelial cells are involved in mediating the processes of coagulation, platelet adhesion, immune function, control of volume and electrolyte content of the intravascular and extravascular spaces. Endothelial dysfunction is associated with proinflammatory, pro-oxidative and prothrombotic changes within the arterial wall as well as increase vessel wall thickness and collagen content. Endothelial dysfunction is thought to be a key event in the development and progression of atherosclerosis and arterial stiffness, and predates clinically obvious vascular complications. Endothelial dysfunction is of prognostic significance in detecting vascular disease and predicting adverse vascular events. Risk factors for atherosclerosis and vascular disease/events are associated with endothelial dysfunction. Endothelial damage also contributes to the development of renal injury and/or chronic or progressive kidney damages, such as e.g. tubulointerstitial fibrosis, glomerulonephritis, micro- or macroalbuminuria, nephropathy and/or chronic kidney disease or renal failure. There is supporting evidence that oxidative stress does not only contribute to endothelial dysfunction or damage but also to vascular disease.

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to hyperglycaemia and its associated micro- and macrovascular complications or chronic damages, such as e.g. diabetic nephropathy, retinopathy or neuropathy, or macrovascular (e.g. cardiovascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialised World because of diabetes induced complications and is associated with a two to five fold increase in cardiovascular disease risk. Type 1 diabetes mellitus (Type 1 diabetes), also called insulin dependent diabetes mellitus or juvenile diabetes, is a form of diabetes mellitus that results from autoimmune destruction of insulin-producing beta cells of the pancreas. The subsequent lack of insulin leads to increased blood glucose concentrations and increased urinary glucose excretion. The classical symptoms are polyuria, polydipsia, polyphagia, and weight loss. Type 1 diabetes may be fatal unless treated with insulin. Complications from type 1 diabetes are the same or similar to complications from type 2 diabetes.

Large randomized studies have established that intensive and tight glycemic control during early (newly diagnoses to 5 years) stage diabetes has enduring beneficial effects and reduces the risk of diabetic complications, both micro- and macrovascular. However, many patients with diabetes still develop diabetic complications despite receiving intensified glycemic control.

Epidemiological and prospective data support a long-term influence of early (newly diagnosed to 5 years) metabolic control on clinical outcomes. It has been found that hyperglycemia has long-lasting deleterious effects both in type 1 and type 2 diabetes and that glycemic control, if not started at a very early stage of the disease or not intensively or not tightly provided, may not be enough to completely reduce complications.

It has been further found that transient episodes of hyperglycemia (e.g. hyperglycemic events), can induce molecular changes, and that these changes can persist or are irreversible after return to normoglycemia.

Collectively, these data suggest that metabolic memories are stored early in the course of diabetes and that, in certain diabetic conditions, oxidative and/or vascular stresses can persist after glucose normalization. This phenomenon that early glycemic environment, and/or even transient hyperglycemia, is remembered with clinical consequences in the target end organs (e.g. blood vessels, retina, kidney, heart, extremities) has recently been termed as 'metabolic memory.'

Potential mechanisms for propagating this 'memory' are certain epigenetic changes, the non-enzymatic glycation of cellular proteins and lipids (e.g. formation of advanced glycation end-products), oxidatively modified atherogenic lipoproteins, and/or an excess of cellular reactive oxygen and nitrogen species (RONS), in particular originated at the level of glycated-mitochondrial proteins, perhaps acting in concert with one another to maintain stress signalling.

Mitochondria are one of major sources of reactive oxygen species (ROS) in cells.

Mitochondrial dysfunction increases electron leak and the generation of ROS from the mitochondrial respiratory chain (MRC). High levels of glucose and lipids impair the activities of MRC complex enzymes. For example, the MRC enzyme NADPH oxidase generates superoxide from NADPH in cells. Increased NADPH oxidase activity can be detected in diabetic patients.

Further, there is evidence that overproduction of free radicals, such as e.g. reactive oxygen species (ROS), contributes to oxidative and vascular stress after glucose normalization and to developing and/or maintaining the metabolic memory, and thus to the unifying link between hyperglycemia and cellular memory effects, such as e.g. in endothelial dysfunction or other complications of diabetes.

Thus, mainly related to persisting (long-term) oxidative stress induced by or associated with (chronic, early or transient episodes of) hyperglycemia, there are certain metabolic conditions in that, even normalizing glycemia, a long-term persistent activation of many pathways involved in the pathogenesis of diabetic complications can still be present. One of the major findings in the course of diabetes has thereby been the demonstration that even in normoglycemia and independent of the actual glycemic levels an overproduction of free radicals can still be evident. For example, endothelial dysfunction (a causative marker of diabetic vascular complications) can persist even after normalizing glycemia. However, there is evidence that combining antioxidant therapy with normalization of glycemia can be used to almost interrupt endothelial dysfunction.

Therefore, treating oxidative and/or vascular stress particularly beyond glycemic control, such as by the reduction of cellular reactive species and/or of glycation (e.g. by inhibition of the production of free oxygen and nitrogen radicals), preferably independently of glycemic status, may beneficially modulate, reduce, block or protect against the memory' effect of hyperglycemia and reduce the risk, prevent, treat or delay the onset of long-term diabetic complications, particularly such ones which are associated with or induced by oxidative stress, in patients in need thereof.

Standard therapy of type 1 diabetes is insulin treatment. Therapies for type 1 diabetes are for example described in WO 2012/062698.

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required.

But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioration in metabolic control despite treatment and do not sufficiently control metabolic status especially over long-term and thus fail to achieve and to maintain glycemic control in advanced or late stage type 2 diabetes, including diabetes with inadequate glycemic control despite conventional oral or non-oral antidiabetic medication.

Therefore, although intensive treatment of hyperglycemia can reduce the incidence of chronic damages, many patients with type 2 diabetes remain inadequately treated, partly because of limitations in long term efficacy, tolerability and dosing inconvenience of conventional antihyperglycemic therapies.

This high incidence of therapeutic failure is a major contributor to the high rate of long-term hyperglycemia-associated complications or chronic damages (including micro- and makrovascular complications such as e.g. diabetic nephrophathy, retinopathy or neuropathy, or cardiovascular complications such as e.g. myocardial infarction, stroke or vascular mortality or morbidity) in patients with type 2 diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, DPP-4 inhibitors, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting) and, most seriously (but rare), pancreatitis.

Therefore, it remains a need in the art to provide efficacious, safe and tolerable antidiabetic therapies.

Further, within the therapy of type 2 diabetes, it is a need for treating the condition effectively, avoiding the complications inherent to the condition, and delaying disease progression, e.g. in order to achieve a long-lasting therapeutic benefit.

Furthermore, it remains a need that antidiabetic treatments not only prevent the long-term Moreover, it remains a need to provide prevention or reduction of risk for adverse effects associated with conventional antidiabetic therapies.

SGLT2 inhibitors (sodium-glucose co-transporter 2) represent a novel class of agents that are being developed for the treatment or improvement in glycemic control in patients with type 2 diabetes. Glucopyranosyl-substituted benzene derivative are described as SGLT2 inhibitors, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient. There are at least 3 SGLT isoforms that differ in their expression pattern as well as in their physico-chemical properties. SGLT2 is exclusively expressed in the kidney, whereas SGLT1 is expressed additionally in other tissues like intestine, colon, skeletal and cardiac muscle. SGLT3 has been found to be a glucose sensor in interstitial cells of the intestine without any transport function. Potentially, other related, but not yet characterized genes, may contribute further to renal glucose reuptake. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentration and to glucosuria.

Empagliflozin is a novel SGLT2 inhibitor that is described for the treatment or improvement in glycemic control in patients with type 2 diabetes mellitus, for example in WO 05/092877, WO 06/117359, WO 06/120208, WO 2010/092126, WO 2010/092123, WO 2011/039107, WO 2011/039108.

Accordingly, in a particular embodiment, a SGLT-2 inhibitor within the meaning of this invention is empagliflozin.

Further, the present invention relates to a therapeutic (treatment or prevention) method as described herein, said method comprising administering an effective amount of a SGLT-2 inhibitor as described herein and, optionally, one or more other active or therapeutic agents as described herein to the patient in need thereof.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, a DPP-4 inhibitor, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), metformin/DPP-4 inhibitor, sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of diabetic patients within the meaning of this invention refers to type 1 or type 2 diabetes patients with or at risk of developing micro- or macrovascular diabetic complications, such as e.g. described herein (e.g. such at risk patients as described as follows).

A further embodiment of the diabetes patients which may be amenable to the therapies of this invention may include, without being limited, those type 1 or type 2 diabetes patients with or at risk of developing retinal complications, such as diabetic retinopathy.

A further embodiment of the diabetes patients which may be amenable to the therapies of this invention may include, without being limited, those type 1 or type 2 diabetes patients with or at risk of developing macrovascular complications, such as myocardial infarction, coronary artery disease, ischemic or hemorrhagic stroke, and/or peripheral occlusive arterial disease.

A further embodiment of the diabetes patients which may be amenable to the therapies of this invention may include, without being limited, those type 1 or type 2 diabetes patients with or at risk of cardiovascular diseases or events (such as e.g. those cardiovascular risk patients described herein).

A further embodiment of the diabetes patients which may be amenable to the therapies of this invention may include, without being limited, those diabetes patients (especially type 2 diabetes) with advanced age and/or with advanced diabetes disease, such as e.g. patients on insulin treatment, patients on triple antidiabetic oral therapy, patients with pre-existing cardiovascular events and/or patients with advanced disease duration (e.g. >/=5 to 10 years).

According to one aspect of the present invention a patient is a type 1 or type 2 diabetes patient.

In one embodiment, the patient is a type 1 or type 2 diabetes patient with one or more cardiovascular risk factors selected from A), B), C) and D):

A) previous or existing vascular disease selected from myocardial infarction, coronary artery disease, percutaneous coronary intervention, coronary artery by-pass grafting, ischemic or hemorrhagic stroke, congestive heart failure, and peripheral occlusive arterial disease, B) advanced age >/=60-70 years, and C) one or more cardiovascular risk factors selected from
- advanced type 2 diabetes mellitus >10 years duration,
- hypertension,
- current daily cigarette smoking,
- dyslipidemia,
- obesity,
- age >/=40,
- metabolic syndrome, hyperinsulinemia or insulin resistance, and
- hyperuricemia, erectile dysfunction, polycystic ovary syndrome, sleep apnea, or family history of vascular disease or cardiomyopathy in first-degree relative;

D) one or more of the following:
- confirmed history of myocardial infarction,
- unstable angina with documented multivessel coronary disease or positive stress test,
- multivessel Percutaneous Coronary Intervention,
- multivessel Coronary Artery By-pass Grafting (CABG),
- history of ischemic or hemorrhagic stroke,
- peripheral occlusive arterial disease.

In a further aspect of the present invention, a patient having at risk of a cardiovascular disease is defined as having at least one of the following:

Confirmed history of myocardial infarction; or

Evidence of multivessel coronary artery disease, in 2 or more major coronary arteries, irrespective of the revascularization status, i.e.
  a) Either the presence of a significant stenosis (imaging evidence of at least 50% narrowing of the luminal diameter measured during a coronary angiography or a multi-sliced computed tomography angiography), in 2 or more major coronary arteries,
  b) Or a previous revascularisation (percutaneous transluminal coronary angioplasty with or without stent, or coronary artery bypass grafting), in 2 or more major coronary arteries,
  c) Or the combination of previous revascularisation in one major coronary artery (percutaneous transluminal coronary angioplasty with or without stent, or coronary artery bypass grafting), and the presence of a significant stenosis in another major coronary artery (imaging evidence of at least 50% narrowing of the luminal diameter measured during a coronary angiography or a multi-sliced computed tomography angiography),
  Note: A disease affecting the left main coronary artery is considered as a 2-vessel disease.

Evidence of a single vessel coronary artery disease with:
  a) The presence of a significant stenosis i.e. the imaging evidence of at least 50% narrowing of the luminal diameter of one major coronary artery in patients not subsequently successfully revascularised (measured during a coronary angiography or a multi-sliced computed tomography angiography)
  b) And at least one of the following (either (i) or (ii)):
    i. A positive non invasive stress test, confirmed by either:
      1. A positive exercise tolerance test in patients without a complete left bundle branch block, Wolff-Parkinson-White syndrome, or paced ventricular rhythm, or
      2. A positive stress echocardiography showing regional systolic wall motion abnormalities, or
      3. A positive scintigraphic test showing stress-induced ischemia, i.e. the development of transient perfusion defects during myocardial perfusion imaging;
    ii. Or patient discharged from hospital with a documented diagnosis of unstable angina within 12 months prior to selection.

Episode of unstable angina with confirmed evidence of coronary multivessel or single vessel disease as defined above.

History of ischemic or haemorrhagic stroke

Presence of peripheral artery disease (symptomatic or not) documented by either: previous limb angioplasty, stenting or bypass surgery; or previous limb or foot amputation due to circulatory insufficiency; or angiographic evidence of significant (>50%) peripheral artery stenosis in at least one limb; or evidence from a non-invasive measurement of significant (>50% or as reported as hemodynamically significant) peripheral artery stenosis in at least one limb; or ankle brachial index of <0.9 in at least one limb.

In a further aspect of the present invention, a patient having at risk of a cardiovascular disease is defined as having at least one of the following:
  a) Confirmed history of myocardial infarction,
  b) Unstable angina with documented multivessel coronary disease (at least two major coronary arteries in angiogram) or positive stress test (ST segment depression>=2 mm or a positive nuclear perfusion scintigram),
  c) Multivessel Percutaneous Coronary Intervention (PCI), d) Multivessel Coronary Artery By-pass Grafting (CABG), including with recurrent angina following surgery,
e) History of ischemic or hemorrhagic stroke,
f) Peripheral occlusive arterial disease (previous limb bypass surgery or percutaneous transluminal angioplasty; previous limb or foot amputation due to circulatory insufficiency, angiographic or imaging detected (for example: ultrasound, Magnetic Resonance Imaging) significant vessel stenosis of major limb arteries).

Moreover, the present invention relates to a certain SGLT-2 inhibitor for use in a method of preventing, reducing the risk of or delaying the occurrence of cardiovascular events, such as cardiovascular death, (fatal or non-fatal) myocardial infarction (e.g. silent or non-silent MI), (fatal or non-fatal) stroke, or hospitalisation (e.g. for acute coronary syndrome, leg amputation, (urgent) revascularization procedures, heart failure or for unstable angina pectoris), preferably in type 1 or type 2 diabetes patients, particularly in those type 1 or type 2 diabetes patients being at risk of cardiovascular events, such as type 1 or type 2 diabetes patients with one or more risk factors selected from A), B), C) and D):
A) previous or existing vascular disease (such as e.g. myocardial infarction (e.g. silent or non-silent), coronary artery disease, percutaneous coronary intervention, coronary artery by-pass grafting, ischemic or hemorrhagic stroke, congestive heart failure (e.g. NYHA class I, II, III or IV, e.g. left ventricular function<40%), or peripheral occlusive arterial disease),
B) advanced age (such as e.g. age >1=60-70 years), and
C) one or more cardiovascular risk factors selected from
  advanced type 1 or type 2 diabetes mellitus (such as e.g. >10 years duration),
  hypertension (such as e.g. >130/80 mm Hg, or systolic blood pressure>140 mmHg or on at least one blood pressure lowering treatment),
  current daily cigarette smoking,
  dyslipidemia (such as e.g. atherogenic dyslipidemia, postprandial lipemia, or high level of LDL cholersterol (e.g. LDL cholesterol>1=130-135 mg/dL), low level of HDL cholesterol (e.g. <35-40 mg/dL in men or <45-50 mg/dL in women) and/or high level of triglycerides (e.g. >200-400 mg/dL) in the blood, or on at least one treatment for lipid abnormality),
  obesity (such as e.g. abdominal and/or visceral obesity, or body mass index>/=45 kg/m2),
  age >/=40,
  metabolic syndrome, hyperinsulinemia or insulin resistance, and
  hyperuricemia, erectile dysfunction, polycystic ovary syndrome, sleep apnea, or family history of vascular disease or cardiomyopathy in first-degree relative,
D) one or more of the following:
  confirmed history of myocardial infarction,
  unstable angina with documented multivessel coronary disease or positive stress test,
  multivessel Percutaneous Coronary Intervention,
  multivessel Coronary Artery By-pass Grafting (CABG),
  history of ischemic or hemorrhagic stroke,
  peripheral occlusive arterial disease,
said method comprising administering a therapeutically effective amount of the SGLT-2 inhibitor, optionally in combination with one or more other therapeutic substances, to the patient.

In a further aspect, the present invention relates to a certain SGLT-2 inhibitor for use in a method of reducing arterial stiffness in a patient. In one aspect, the patient is a patient according to the present invention, in particular a patient with type 1 or type 2 diabetes or pre-diabetes. Increased arterial stiffness is associated with an increased risk of cardiovascular events and the effect of empagliflozin on arterial stiffness is for example shown in the Examples hereinbelow.

The present invention further relates to a pharmaceutical composition comprising a certain SGLT-2 inhibitor as defined herein, empagliflozin, for use in the therapies described herein.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 10 to 17 years, preferably of age 13 to 17 years. It is assumed that in a adolescent population the administration of the pharmaceutical composition according to the invention a very good HbA1c lowering and a very good lowering of the fasting plasma glucose can be seen. In addition it is assumed that in an adolescent population, in particular in overweight and/or obese patients, a pronounced weight loss can be observed.

As described hereinbefore by the administration of the pharmaceutical composition according to this invention and in particular in view of the high SGLT2 inhibitory activity of the SGLT2 inhibitors therein, excessive blood glucose is excreted through the urine of the patient, so that no gain in weight or even a reduction in body weight may result. Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy or a therapy using only two of the combination partners.

The pharmaceutical composition according to this invention and in particular the SGLT2 inhibitor therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

Furthermore, the method and/or use according to this invention is advantageously applicable in those patients who show one, two or more of the following conditions:
(a) a fasting blood glucose or serum glucose concentration greater than 100 mg/dL, in particular greater than 125 mg/dL;
(b) a postprandial plasma glucose equal to or greater than 140 mg/dL;

(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 1 or type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that an SGLT2 inhibitor as defined hereinbefore and hereinafter is administered to the patient.

According to another preferred embodiment of the present invention, there is provided a method for improving glycemic control in patients, in particular in adult patients, with type 2 diabetes mellitus as an adjunct to diet and exercise.

It can be found that by using a pharmaceutical composition according to this invention, an improvement of the glycemic control can be achieved even in those patients who have insufficient glycemic control in particular despite treatment with an antidiabetic drug, for example despite maximal recommended or tolerated dose of oral monotherapy with metformin. A maximal recommended dose with regard to metformin is for example 2000 mg per day or 850 mg three times a day or any equivalent thereof.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with another antidiabetic agent, in particular despite oral monotherapy at a maximal tolerated dose of the other antidiabetic agent.

The lowering of the blood glucose level by the administration of an SGLT2 inhibitor according to this invention is insulin-independent. Therefore, a pharmaceutical composition according to this invention is particularly suitable in the treatment of patients who are diagnosed having one or more of the following conditions
  insulin resistance,
  hyperinsulinemia,
  pre-diabetes,
  type 2 diabetes mellitus, particular having a late stage type 2 diabetes mellitus,
  type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level 150 mg/dL,
(c) HDL-cholesterol blood level<40 mg/dL in female patients and <50 mg/dL in male patients,
(d) a systolic blood pressure 130 mm Hg and a diastolic blood pressure 85 mm Hg,
(e) a fasting blood glucose level 100 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

Furthermore, a pharmaceutical composition according to this invention is particularly suitable in the treatment of patients after organ transplantation, in particular those patients who are diagnosed having one or more of the following conditions
(a) a higher age, in particular above 50 years,
(b) male gender;
(c) overweight, obesity (including class I, II and/or III obesity), visceral obesity and/or abdominal obesity,
(d) pre-transplant diabetes,
(e) immunosuppression therapy.

Furthermore, a pharmaceutical composition according to this invention is particularly suitable in the treatment of patients who are diagnosed having one or more of the following conditions:
(a) hyponatremia, in particular chronicle hyponatremia;
(b) water intoxication;
(c) water retention;
(d) plasma sodium concentration below 135 mmol/L.

The patient may be a diabetic or non-diabetic mammal, in particular human.

Furthermore, a pharmaceutical composition according to this invention is particularly suitable in the treatment of patients who are diagnosed having one or more of the following conditions:
(a) high serum uric acid levels, in particular greater than 6.0 mg/dL (357 µmol/L);
(b) a history of gouty arthritis, in particular recurrent gouty arthritis;
(c) kidney stones, in particular recurrent kidney stones;
(d) a high propensity for kidney stone formation.

In certain embodiments, the patients which may be amenable to the therapies of this invention may have or are at-risk of one or more of the following diseases, disorders or conditions: type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyper-NEFA-emia, postprandial lipemia, hypertension, atherosclerosis, endothelial dysfunction, osteoporosis, chronic systemic inflammation, non alcoholic fatty liver disease (NAFLD), polycystic ovarian syndrome, metabolic syndrome, nephropathy, micro- or macroalbuminuria, proteinuria, retinopathy, cataracts, neuropathy, learning or memory impairment, neurodegenerative or cognitive disorders, cardiovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries, (renal, cardiac, cerebral or hepatic) fibrosis, (renal, cardiac, cerebral or hepatic) vascular remodeling; a diabetic disease, especially type 2 diabetes, mellitus may be preferred (e.g. as underlying disease).

In a further embodiment, the patients which may be amenable to the therapies of this invention have a diabetic disease, especially type 2 diabetes mellitus, and may have or are at-risk of one or more other diseases, disorders or conditions, such as e.g. selected from those mentioned immediately above.

In further embodiments, the present invention also relates to the effect of certain SGLT-2 inhibitors, in particular empagliflozin, on beta-cells and/or on the function of beta-cells, for example in patients having latent autoimmune diabetes in adults (LADA).

Accordingly, in one embodiment, the present invention relates to certain SGLT-2 inhibitors, in particular empagliflozin, for use in preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient having latent autoimmune diabetes in adults (LADA).

In a further embodiment, the present invention relates to certain SGLT-2 inhibitors, in particular empagliflozin, for use in preserving pancreatic beta cells and/or their function in a patient having latent autoimmune diabetes in adults (LADA).

In a further embodiment, the present invention relates to certain SGLT-2 inhibitors, in particular empagliflozin, for use in stimulating and/or protecting the functionality of pancreatic insulin secretion in a patient having latent autoimmune diabetes in adults (LADA).

Usually three criteria are needed fulfilled for diagnosis of LADA:
1) adult age at onset of diabetes (>30 years),
2) the presence of circulating islet autoantibodies (markers of beta cell autoimmunity to distinguish LADA from T2DM, e.g. islet cell antibodies (ICA, against cytoplasmic proteins in the beta cell, islet-cell cytoplasm), antibodies to glutamic acid decarboxylase (GAD-65, anti-GAD), insulin autoantibodies (IAA), and/or IA-2A antibodies to the intracytoplasmatic domain of the tyrosine phosphatase-like protein IA-2), and
3) lack of a requirement for insulin for at least 6 months after diagnosis (to distinguish LADA from classic T1 DM).

However, alternative definitions of LADA include GAD (glutamic acid decarboxylase) antibody titer≥0.08 U/mL and 1) lifestyle and oral therapy or 2) insulin treatment started later than 12 months after diagnosis or 3) insulin therapy started before 12 months after diagnosis, but with fasting C-peptide levels>150 pmol/l.

C-peptide originates from proinsulin and is produced in the body along with insulin. It is an accepted biomarker for proof of beta-cell preservation. Persons with LADA typically have low, although sometimes moderate, levels of C-peptide as the disease progresses.

One prerequisite in the definition is the presence of one or more circulating autoantibodies. For this reasons it is sometimes argued that LADA is just a "low-titer T1 DM condition".

However, the LADA population often shares phenotypical traits with T2DM, more so than with T1 DM; therefore LADA etiologically may represent a unique disease entity that is characterized by a more rapid decline of β-cell function than common T2DM.

It has been demonstrated, in several studies, that insulin dependency occurs at higher rate in LADA than in subjects with common T2DM.

Accordingly, in one aspect, a patient having LADA according to the present invention is a patient in whom one or more autoantibodies selected from GAD (GAD-65, anti-GAD), ICA, IA-2A, ZnT8 (anti-ZnT8) and IAA are present, and in one aspect, in a method or use according to the present invention a patient having LADA is a patient in whom one or more autoantibodies selected from GAD (GAD-65, anti-GAD), ICA, IA-2A, ZnT8 (anti-ZnT8).

One assumes that the LADA prevalence in a general type 2 diabetes population is at least 5-10%. Moreover, adults with LADA are frequently initially misdiagnosed as having type 2 diabetes, based on age; not etiology. In a survey conducted by Australia's Type 1 Diabetes Network, one third of all Australians with type 1 diabetes reported being initially misdiagnosed as having the more common type 2 diabetes mellitus.

Currently, there is no "gold standard" for LADA treatment or management. In general, the treatment of LADA should focus not only on controlling glycemia and preventing the onset of any complications, but also allow preservation of residual beta cell function. Insulin therapy in LADA is often efficacious; but might be of most benefit in patients with both a high titer of GAD (>10 U/mL) and preserved insulin secretion (C-peptide>10 ng/mL). This also seems to apply to thiazolidinediones (glitazones), in particular if combined with insulin when islet beta cell function is preserved. Sulfonylureas (SUs) (and glinides) have in some studies been shown to be detrimental on beta cell function in LADA. This is supported by that metabolic control by SUs when compared to insulin also is often less.

Accordingly, in a further embodiment, the present invention relates to certain SGLT-2 inhibitors, in particular empagliflozin, for use in treating and/or preventing LADA (latent autoimmune diabetes of adults), particularly in those patients having LADA in whom one or more autoantibodies selected from GAD (GAD-65, anti-GAD), ICA, IA-2A, ZnT8 (anti-ZnT8) and IAA are present.

Within the scope of the present invention it has now been found that certain SGLT-2 inhibitors as defined herein, optionally in combination with one or more other therapeutic substances (e.g. selected from those described herein), as well as pharmaceutical combinations, compositions or combined uses according to this invention of such SGLT-2 inhibitors as defined herein have properties, which make them suitable for the purpose of this invention and/or for fulfilling one or more of above needs.

The effect of empagliflozin on cardiovascular diseases, in particular on the risk of a cardiovascular event, for example such as defined herein, is for example determined as described in the Examples hereinbelow.

The effect of empagliflozin on beta-cells and/or on the function of beta-cells is for example determined as described in the Examples hereinbelow.

The present invention thus relates to a certain SGLT-2 inhibitor as defined herein, preferably empagliflozin, for use in the therapies described herein.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor according to this invention is included in the pharmaceutical composition or dosage form in an amount sufficient that by its administration the glycemic control in the patient to be treated is improved.

For the treatment of hyperuricemia or hyperuricemia associated conditions the SGLT2 inhibitor according to this invention is included in the pharmaceutical composition or dosage form in an amount sufficient that is sufficient to treat hyperuricemia without disturbing the patient's plasma glucose homeostasis, in particular without inducing hypoglycemia.

For the treatment or prevention of kidney stones the SGLT2 inhibitor according to this invention is included in the pharmaceutical composition or dosage form in an amount sufficient that is sufficient to treat or prevent kidney stones without disturbing the patient's plasma glucose homeostasis, in particular without inducing hypoglycemia.

For the treatment of hyponatremia and associated conditions the SGLT2 inhibitor according to this invention is included in the pharmaceutical composition or dosage form in an amount sufficient that is sufficient to treat hyponatremia or the associated conditions without disturbing the patient's plasma glucose homeostasis, in particular without inducing hypoglycemia.

In the following preferred ranges of the amount of the SGLT2 inhibitor to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. Within the scope of the present invention, the pharmaceutical composition is preferably administered orally. Other forms of administration are possible and described hereinafter. Preferably the one or more dosage forms comprising the SGLT2 inhibitor is oral or usually well known.

In general, the amount of the SGLT2 inhibitor in the pharmaceutical composition and methods according to this invention is preferably the amount usually recommended for a monotherapy using said SGLT2 inhibitor.

The preferred dosage range of the SGLT2 inhibitor is in the range from 0.5 mg to 200 mg, even more preferably from 1 to 100 mg, most preferably from 1 to 50 mg per day. In one aspect, a preferred dosage of the SGLT2 inhibitor empagliflozin is 10 mg or 25 mg per day. The oral administration is preferred. Therefore, a pharmaceutical composition may comprise the hereinbefore mentioned amounts, in particular from 1 to 50 mg or 1 to 25 mg. Particular dosage strengths (e.g. per tablet or capsule) are for example 1, 2.5, 5, 7.5, 10, 12.5, 15, 20, 25 or 50 mg of the SGLT2 inhibitor, in particular empagliflozin. In one aspect, a pharmaceutical composition comprises 10 mg or 25 mg of empagliflozin. The application of the active ingredient may occur up to three times a day, preferably one or two times a day, most preferably once a day.

A pharmaceutical composition which is present as a separate or multiple dosage form, preferably as a kit of parts, is useful in combination therapy to flexibly suit the individual therapeutic needs of the patient.

According to a first embodiment a preferred kit of parts comprises a containment containing a dosage form comprising the SGLT2 inhibitor and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

According to a first embodiment a manufacture comprises (a) a pharmaceutical composition comprising a SGLT2 inhibitor according to the present invention and (b) a label or package insert which comprises instructions that the medicament is to be administered.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, sub-cutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to empagliflozin an advantageous crystalline form is described in the international patent application WO 2006/117359 which hereby is incorporated herein in its entirety.

The active ingredients may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

Pharmaceutical compositions or combinations for use in these therapies comprising the SGLT-2 inhibitor as defined herein optionally together with one or more other active substances are also contemplated.

Further, the present invention relates to the SGLT-2 inhibitors, optionally in combination with one, two or more further active agents, each as defined herein, for use in the therapies as described herein.

Further, the present invention relates to the use of the SGLT-2 inhibitors, optionally in combination with one, two or more further active agents, each as defined herein, for preparing pharmaceutical compositions which are suitable for the treatment and/or prevention purposes of this invention.

The present invention further relates to a pharmaceutical composition comprising a certain SGLT-2 inhibitor as defined herein, preferably empagliflozin, and metformin, for use in the therapies described herein.

The present invention further relates to a combination comprising a certain SGLT-2 inhibitor (particularly empagliflozin) and one or more other active substances selected from those mentioned herein, e.g. selected from other antidiabetic substances, active substances that lower the blood sugar level, active substances that lower the lipid level in the blood, active substances that raise the HDL level in the blood, active substances that lower blood pressure, active substances that are indicated in the treatment of atherosclerosis or obesity, antiplatelet agents, anticoagulant agents, and vascular endothelial protective agents, e.g. each as described herein; particularly for simultaneous, separate or sequential use in the therapies described herein.

The present invention further relates to a combination comprising a certain SGLT-2 inhibitor (particularly empagliflozin) and one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, GLP-1 or a GLP-1 analogue and a DPP-4 inhibitor, particularly for simultaneous, separate or sequential use in the therapies described herein.

The present invention further relates to a method for treating and/or preventing metabolic disorders, especially type 2 diabetes mellitus and/or conditions related thereto (e.g. diabetic complications) comprising the combined (e.g. simultaneous, separate or sequential) administration of an effective amount of one or more other antidiabetics selected from the group consisting of metformin, a sulphonylurea, nateglinide, repaglinide, a PPAR-gamma-agonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein, including at-risk patient groups.

The present invention further relates to therapies or therapeutic methods described herein, such as e.g. a method for treating and/or preventing metabolic disorders, especially type 2 diabetes mellitus and/or conditions related thereto (e.g. diabetic complications), comprising administering a therapeutically effective amount of empagliflozin and, optionally, one or more other therapeutic agents, such as e.g. antidiabetics selected from the group consisting of metformin, a sulphonylurea, nateglinide, repaglinide, a PPAR-gamma-agonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein (e.g. at-risk patient as described herein).

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

The present invention further relates to a certain SGLT-2 inhibitor as defined herein, preferably empagliflozin, in combination with metformin, for use in the therapies described herein.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

An example of a DPP-4 inhibitor is linagliptin, which is usually given in a dosage of 5 mg per day.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

In one aspect of the present invention, the one or more other therapeutic substances are active substances that lower the blood sugar level, active substances that lower the lipid level in the blood, active substances that raise the HDL level in the blood, active substances that lower blood pressure, active substances that are indicated in the treatment of atherosclerosis or obesity, antiplatelet agents, anticoagulant agents, and vascular endothelial protective agents.

In one aspect, the present invention provides a method of treatment comprising identifying a patient with type 2 diabetes treated with a plurality of medications to treat a cardiovascular disease, administering empagliflozin to said patient; and reducing the number, dosage or regimen of medications to treat a cardiovascular disease in said patient, in particular while continuing to administer empagliflozin to the patient. In one embodiment, the method further comprises monitoring the cardiac health of said patient.

Examples of medications to treat a cardiovascular disease include medications that lower blood, such as for example beta-blockers, diuretics, calcium channel blockers, Angiotensin-Converting Enzyme (ACE) inhibitors and angiotensin II receptor blockers (ARBs).

Examples of medications that lower blood pressure are beta-blockers such as acebutolol, atenolol, Betaxolol, bisoprolol, celiprolol, metoprolol, nebivolol, Propranolol, Timolol and carvedilol; the dosage(s) of some of these medications are for example shown below:

Acebutolol (Sectral), 200 or 400 mg of acebutolol as the hydrochloride salt

Atenolol (Tenormin), 25, 50 and 100 mg tablets for oral administration

Betaxolol (Kerlone), 10-mg and 20-mg tablets for oral administration

Bisoprolol/hydrochlorothiazide (Ziac), 2.5/6 mg, 5/6.25 mg, 10/6.25 mg

Bisoprolol (Zebeta), 5 and 10 mg tablets for oral administration

Metoprolol (Lopressor, Toprol XL), 50- and 100-mg tablets for oral administration and in 5-mL ampuls for intravenous administration Propranolol (Inderal), 10 mg, 20 mg, 40 mg, 60 mg, and 80 mg tablets for oral administration Timolol (Blocadren), 5 mg, 10 mg or 20 mg timolol maleate for oral administration.

Examples of medications that lower blood pressure are diuretics such as Bumetanide, hydrochlorothiazide, chlortalidon, Chlorothiazide, Hydro-chlorothiazide, xipamide, Indapamide, furosemide, piretanide, torasemide, spironolactone, eplerenone, am iloride and triamterene; for example these medications are thiazide diuretics, eg chlorthalidone, HCT, loop diuretics, eg furosemide, torasemide or potassium-sparing diuretics, eg eplerenone, or combination thereof; the dosage(s) of some of these medications are for example shown below:

Amiloride (Midamor), 5 mg of anhydrous amiloride HCl

Bumetanide (Bumex), available as scored tablets, 0.5 mg (light green), 1 mg (yellow) and 2 mg (peach) for oral administration Chlorothiazide (Diuril), Chlorthalidone (Hygroton)

Furosemide (Lasix)

Hydro-chlorothiazide (Esidrix, Hydrodiuril)

Indapamide (Lozol) and Spironolactone (Aldactone)

Eplerenone (Inspra)

Examples of medications that lower blood pressure are calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem.

Examples of medications that lower blood pressure are Angiotensin-Converting Enzyme (ACE) inhibitors such as Benazepril, Captopril, ramipril, lisinopril, Moexipril, cilazapril, quinapril, captopril, enalapril, benazepril, perindopril, fosinopril and trandolapril; the dosage(s) of some of these medications are for example shown below:

Benazepril (Lotensin), 5 mg, 10 mg, 20 mg, and 40 mg for oral administration

Captopril (Capoten), 12.5 mg, 25 mg, 50 mg, and 100 mg as scored tablets for oral administration Enalapril (Vasotec), 2.5 mg, 5 mg, 10 mg, and 20 mg tablets for oral administration Fosinopril (Monopril), for oral administration as 10 mg, 20 mg, and 40 mg tablets Lisinopril (Prinivil, Zestril), 5 mg, 10 mg, and 20 mg tablets for oral administration Moexipril (Univasc), 7.5 mg and 15 mg for oral administration Perindopril (Aceon), 2 mg, 4 mg and 8 mg strengths for oral administration Quinapril (Accupril), 5 mg, 10 mg, 20 mg, or 40 mg of quinapril for oral administration Ramipril (Altace), 1.25 mg, 2.5 mg, 5, mg, 10 mg Trandolapril (Mavik), 1 mg, 2 mg, or 4 mg of trandolapril for oral administration Examples of medications that lower blood pressure are angiotensin II receptor blockers (ARBs) such as telmisartan, candesartan, valsartan, losartan, irbesartan, olmesartan, azilsartan and eprosartan; the dosage(s) of some of these medications are for example shown below:

Candesartan (Atacand), 4 mg, 8 mg, 16 mg, or 32 mg of candesartan cilexetil

Eprosartan (Teveten), 400 mg or 600 mg

Irbesartan (Avapro), 75 mg, 150 mg, or 300 mg of irbesartan.

Losartan (Cozaar), 25 mg, 50 mg or 100 mg of losartan potassium

Telmisartan (Micardis), 40 mg/12.5 mg, 80 mg/12.5 mg, and 80 mg/25 mg telmisartan and hydrochlorothiazide Valsartan (Diovan), 40 mg, 80 mg, 160 mg or 320 mg of valsartan A dosage of telmisartan is usually from 20 mg to 320 mg or 40 mg to 160 mg per day.

Further embodiments, features and advantages of the present invention may become apparent from the following examples. The following examples serve to illustrate, by way of example, the principles of the invention without restricting it.

EXAMPLES

Example 1: Effects of SGLT2 Inhibition on Oxidative Stress, Vessel Wall Thickness and Collagen Content, and Endothelial Dysfunction in STZ-Induced Diabetes Mellitus (Type I) in Rat Type I diabetes in Wistar rats (8 weeks old, 250-300 g) are induced by a single i.v. injection of STZ (60 mg/kg). The blood glucose level is measured 3 days after STZ injection (to test whether diabetes was induced) and on the day of sacrifice. One week after injection empagliflozin (SGLT2-i) was administered with drinking water for additional 7 weeks (10 and 30 mg/kg/d p.o.). Treatment with empagliflozin showed a distinct reduction of blood glucose levels in diabetic rats without influence on loss of weight gain. Isometric tension recordings showed an empagliflozin-dependent normalization of endothelial function in diabetic animals and reduced oxidative stress in aortic vessels and blood, examined by DHE staining of aortic cryosections and PDBu/zymosanA-stimulated chemiluminescence, respectively. Additionally, a tendency of increased NADPH-oxidase activity in heart and a significant reduction of ALDH-2 activity in the liver were observed in diabetic animals, reflecting oxidative stress diminution triggered by empagliflozin therapy. The results are shown in FIGS. 1-13.

FIG. 1A-C: Shows the effect of Empagliflozin on weight gain, blood glucose and glycated hemoglobin (HbA1C) at low dose (10 mg/kg) and high dose (30 mg/kg) given in drinking water.

Figure 2A:
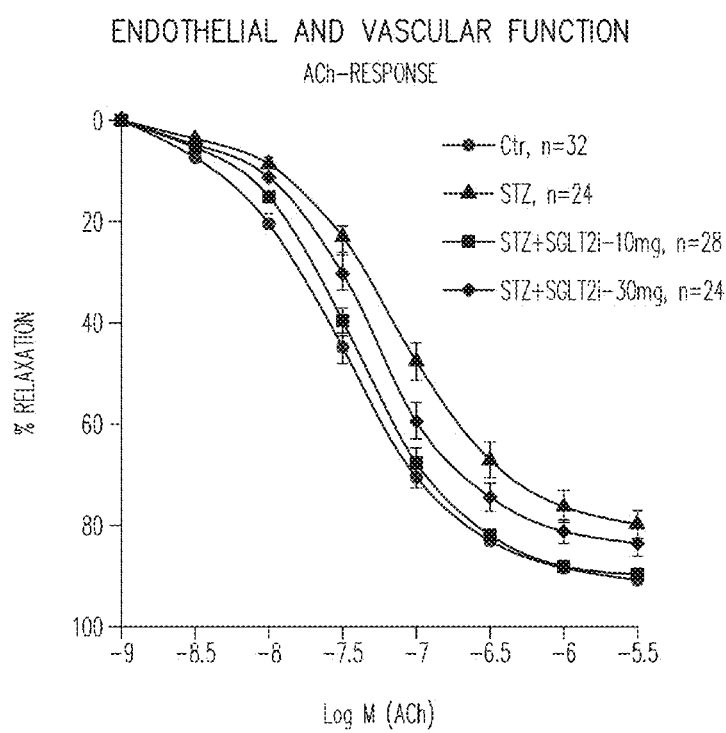
FIGS. 2A and 2B: relaxation (endothelial function) deteriorated in STZ treated (diabetic) animal and after treatment with empagliflozin. The GTN curve on FIG. 2B is the positive control to show that in Nitric oxide supplies, all tissues equivalent showing the integrity of the vessels wall.
Figure 2B:
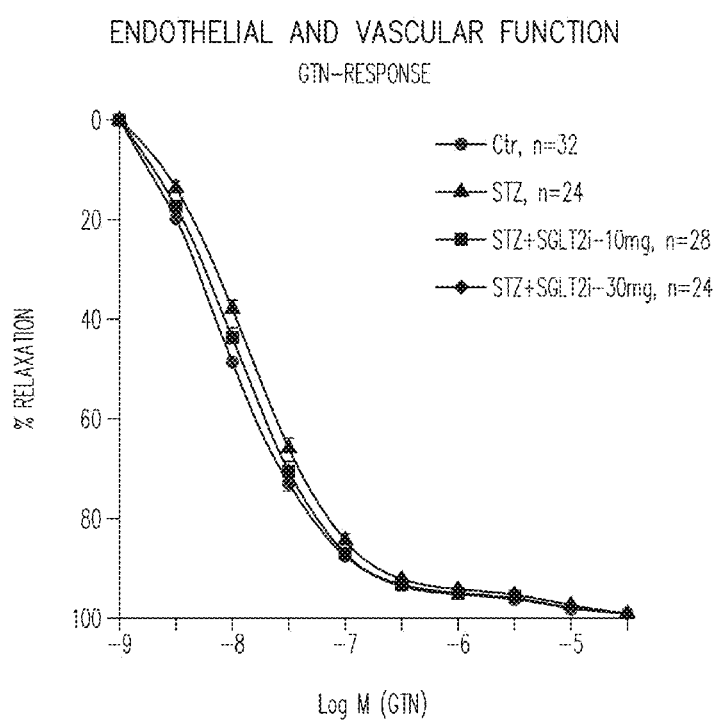
Figure 3:
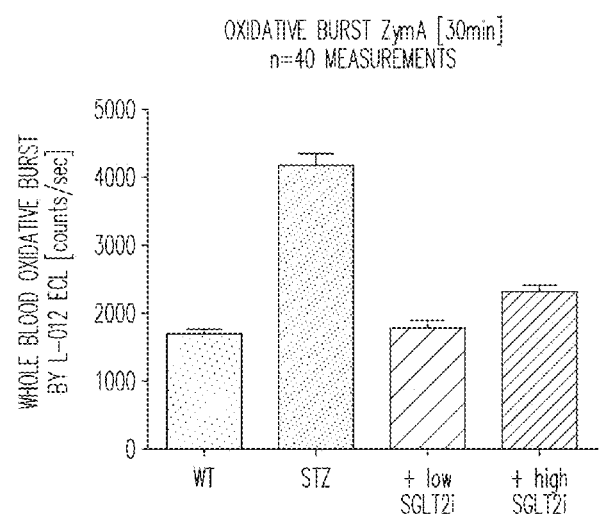
FIG. 3: oxidative burst (leukocyte-derived reactive oxygen species (ROS)) in blood upon ZymA stimulation at 30 minutes.
Figure 4:
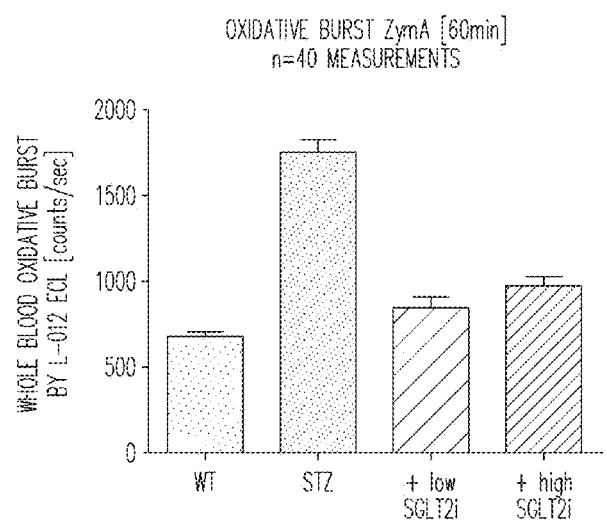
FIG. 4: oxidative burst (leukocyte-derived ROS) in blood upon ZymA stimulation at 60 minutes.
Figure 5:
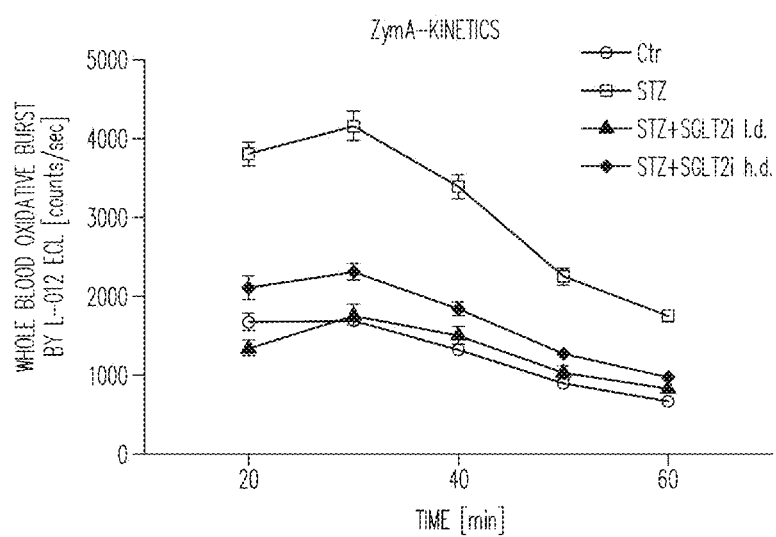
FIG. 5: time course of oxidative burst (leukocyte-derived ROS) in blood upon ZymA stimulation.
Figure 6:
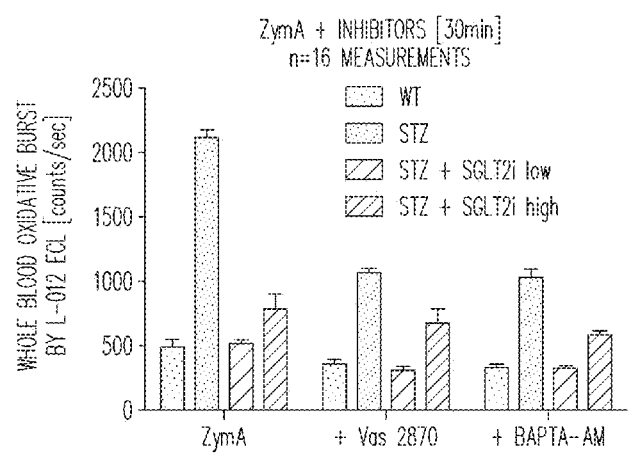
FIG. 6: oxidative burst (leukocyte-derived ROS) in blood upon ZymA stimulation (at 30 minutes) with inhibitors of Nox2 activity (VAS2870) and an intracellular calcium chelator.
Figure 7:
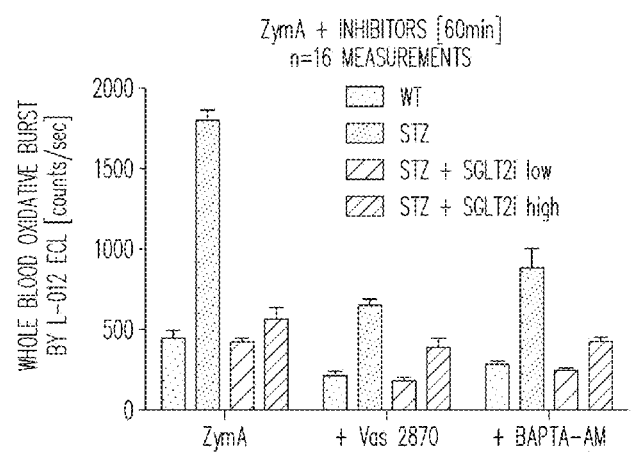
FIG. 7: oxidative burst (leukocyte-derived ROS) in blood upon ZymA stimulation (at 60 minutes) with inhibitors of Nox2 activity (VAS2870) and an intracellular calcium chelator.
Figure 8:
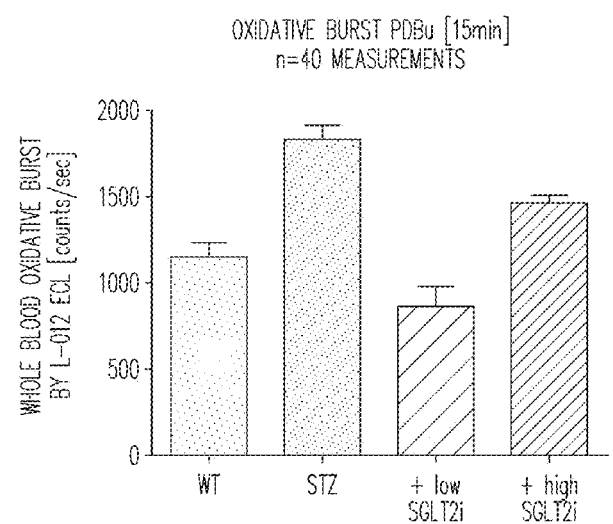
FIG. 8: oxidative burst (leukocyte-derived ROS) in blood upon PDBu stimulation at 15 minutes.
Figure 9:
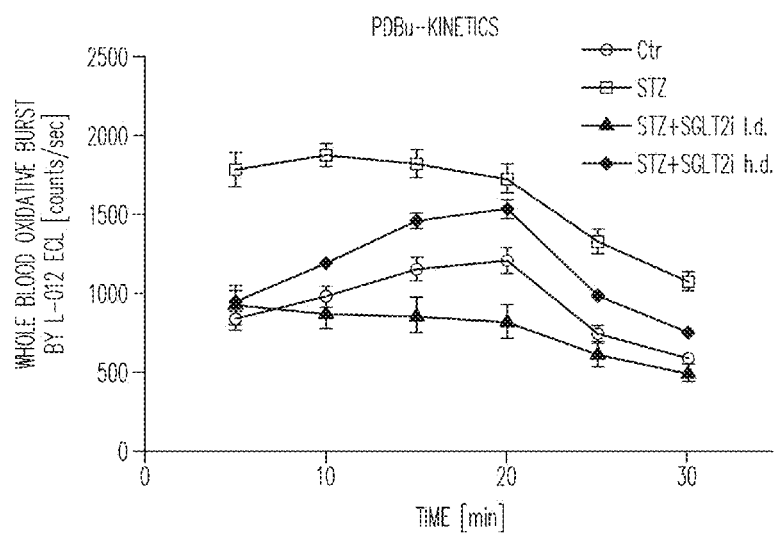
FIG. 9: time course of oxidative burst (leukocyte-derived ROS) in blood upon PDBu stimulation.

FIG. 2: A: Endothelial dependant vasorelaxation. This figure shows the improvement of endothelial function measured with isolated aortic rings after 7 weeks of treatment.

B: Endothelial independent vasorelaxation obtain with glyceryl trinitrate (GTN) a NO donor. This figure shows the capacity of all vessel walls to vasorelax independently of the endothelium demonstrating the absence of deleterious effect of the treatment on smooth muscle cells.

FIGS. 3-9: Quantification of reactive oxygen species of (ROS) from leukocyte upon stimulation with zymosan A (ZymA). After 7 weeks of treatment, ROS production in blood is reduced either with the low or high dose of empagliflozin to level close to none diabetic animal.

Figure 10:
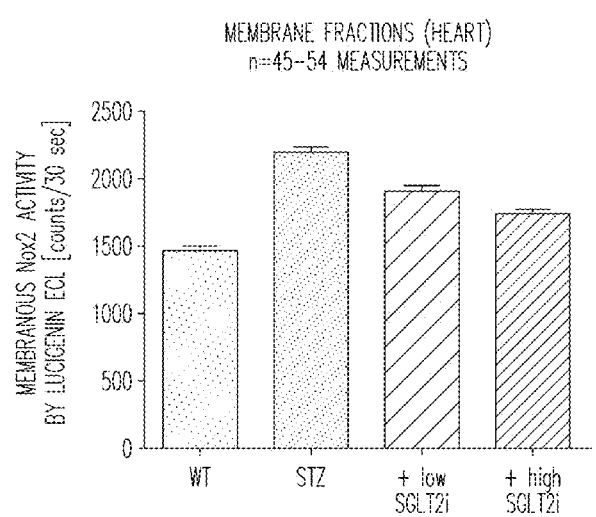
FIG. 10: membranous NADPH oxidase activity.

FIG. 10: Shows that the NADPH oxidase activity in the cardiac tissue, an important source of superoxide is diminished with empagliflozin treatment.

Figure 11A:
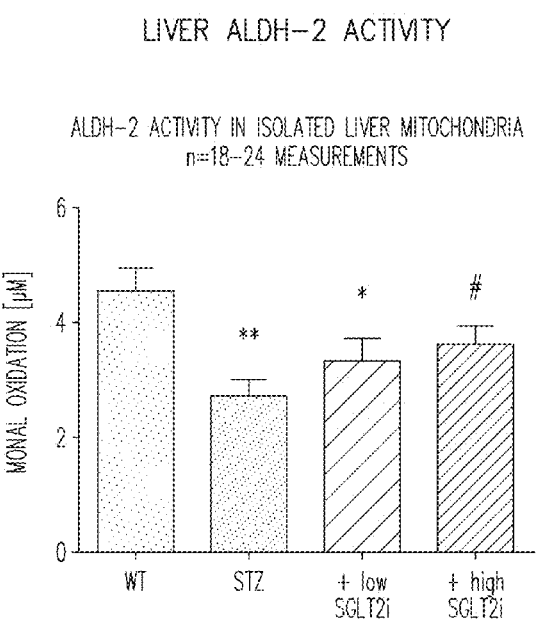
FIGS. 11A and 11B: liver ALDH-2 activity.
Figure 11B:
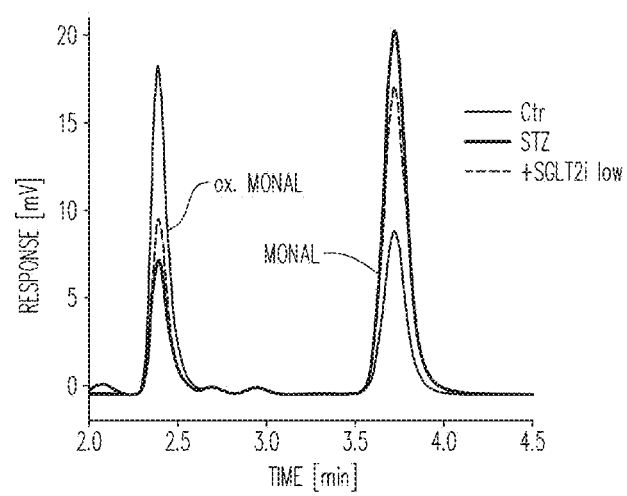

FIG. 11: Shows that the reduction of ALDH-2 activity in diabetic STZ animal is partly restored with empagliflozin treatment.

Figure 12B:
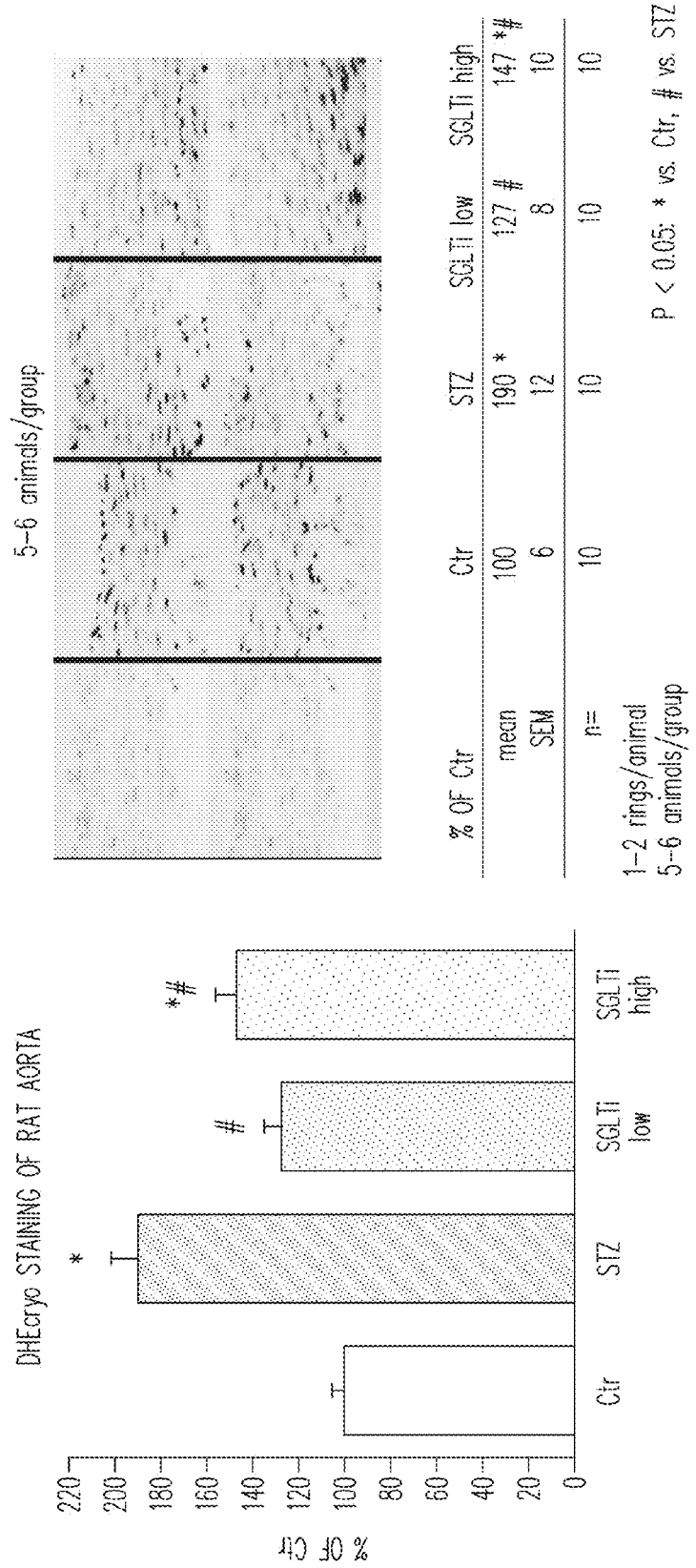
Figure 13A:
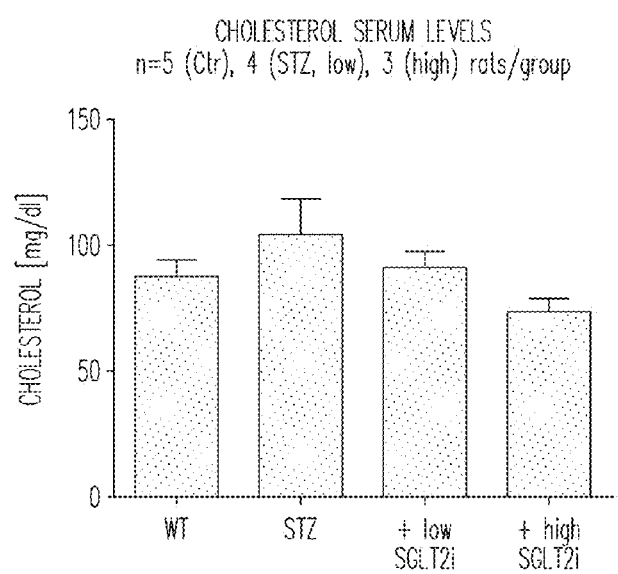
FIGS. 13A-D: serum levels of cholesterol, triglyceride, insulin and interferon-gamma, respectively.
Figure 13B:
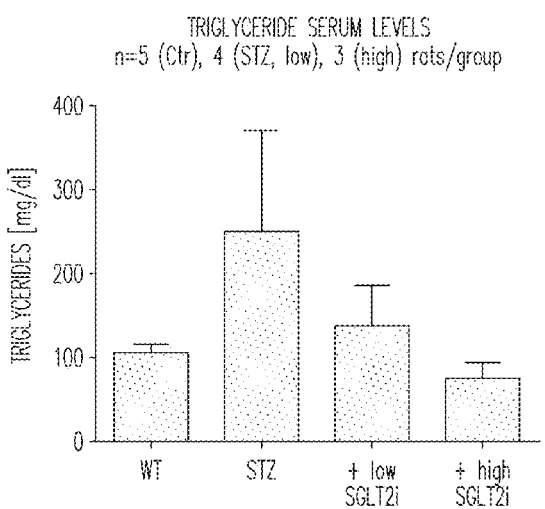
Figure 13C:
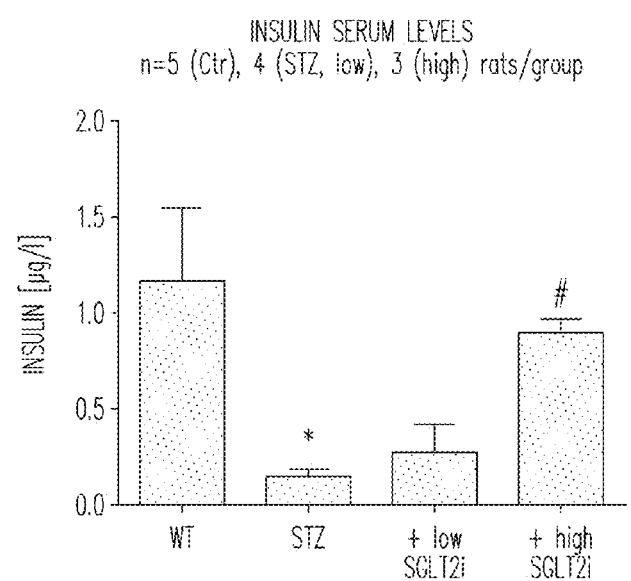
Figure 13D:
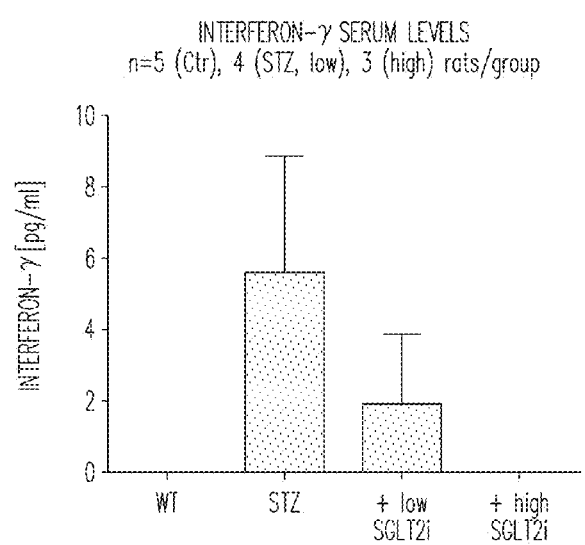

FIGS. 12A and 12B: Shows that the superoxide formation in the vessels of diabetic animals is reduced. FIG. 12A shows results with a partial set of animals, FIG. 12B shows results with all animals.

FIG. 13A-D: Shows the level of plasmatic cholesterol, triglycerides, insulin and Interferon γ in STZ diabetic rats compared to normal rat and in diabetic rat treated with empagliflozin.

While empagliflozin restore insulin level, the elevation of interferon γ (a marker of inflammation) in diabetic rats is highly diminished or suppressed with empagliflozin treatment.

Aortic wall thickness and collagen content were also measured microscopically after sirius red staining. Aortic segments were fixed in parafomaldehyde (4%) and paraffin-embedded. Sirius red staining for vascular fibrosis was performed with paraffin-embedded samples of aortic tissue upon de-paraffination. Afterwards the nuclei were prestained with hemalum. Then samples were stained for 1 hour in 0.1% with Sirius red solution containing saturated picric acid (1.2%). Finally, tissue samples were dehydrated with 70%, 96% and 100% isopropanol and coverslipped with a solution of polymers in xylene. 60-70 measurements were made per sample, n=6-7 animals/groups. The results are shown in FIGS. 16A and 16B.

Figure 16A:
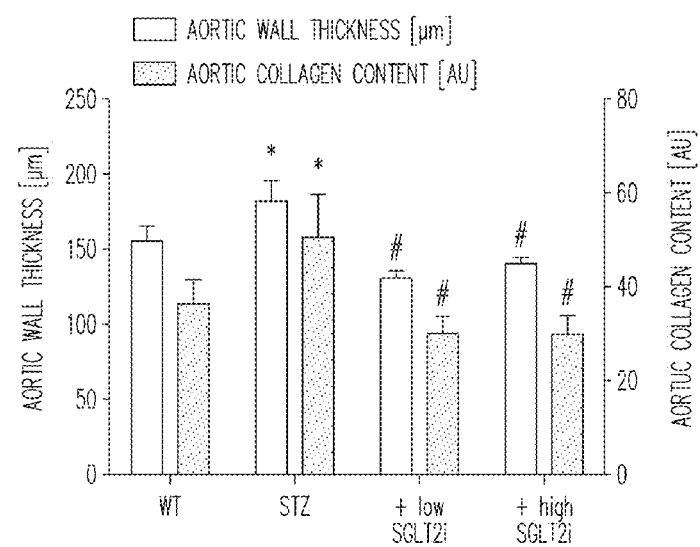
FIGS. 16A and 16B: microscopic determination of aortic wall thickness and collagen content by sirius red staining of aortic paraffinated sections.
Figure 16B:
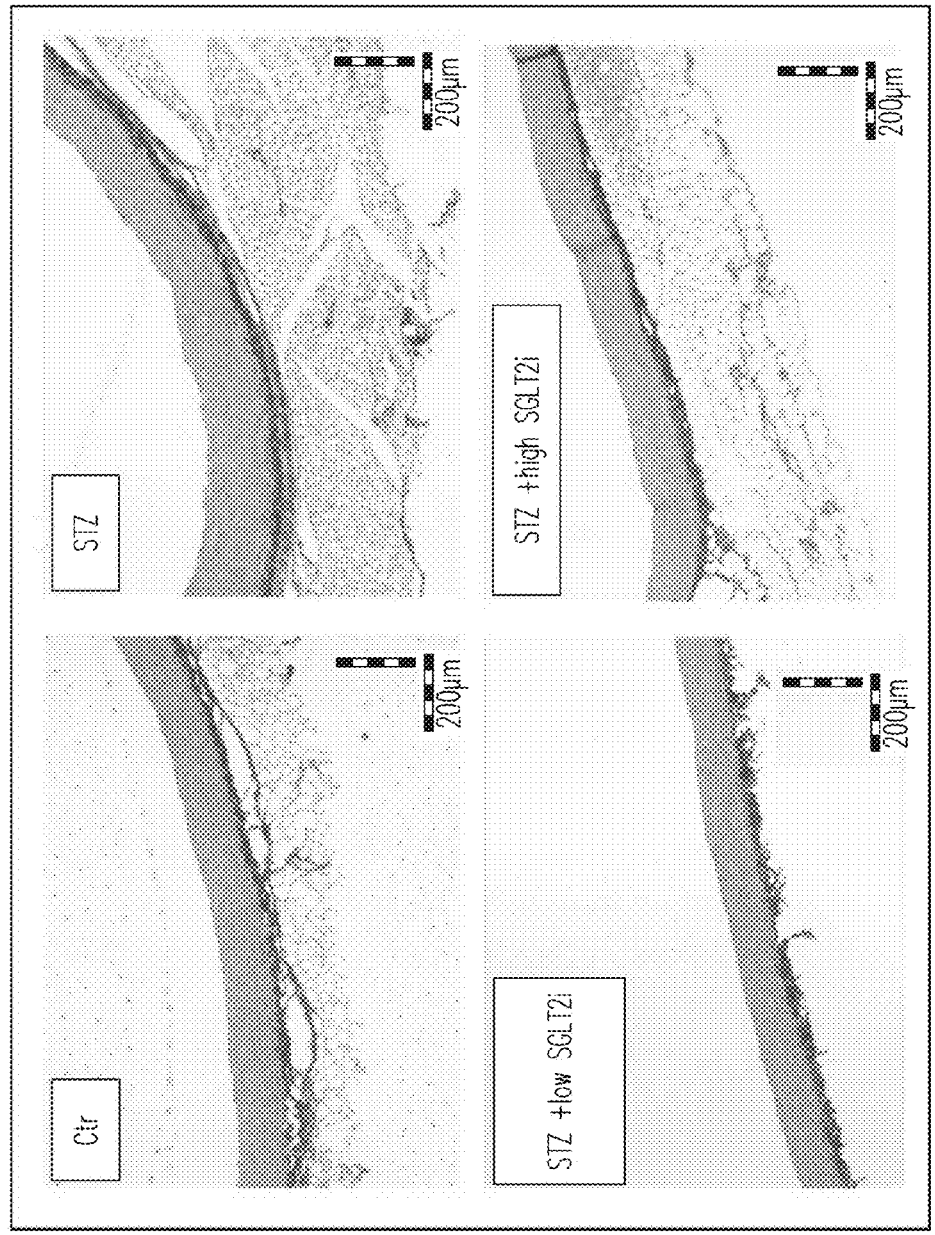

FIGS. 16A and 16B: Microscopic determination of aortic wall thickness and collagen content by sirius red staining of aortic paraffinated sections. Quantification (FIG. 16A) and representative microscope images (FIG. 16B). Aortic wall thickness and collagen content was slightly increased in diabetic rats and was normalized by empagliflozin treatment.

Example 2: Measurement of Hourly Blood Pressure

Figure 14:
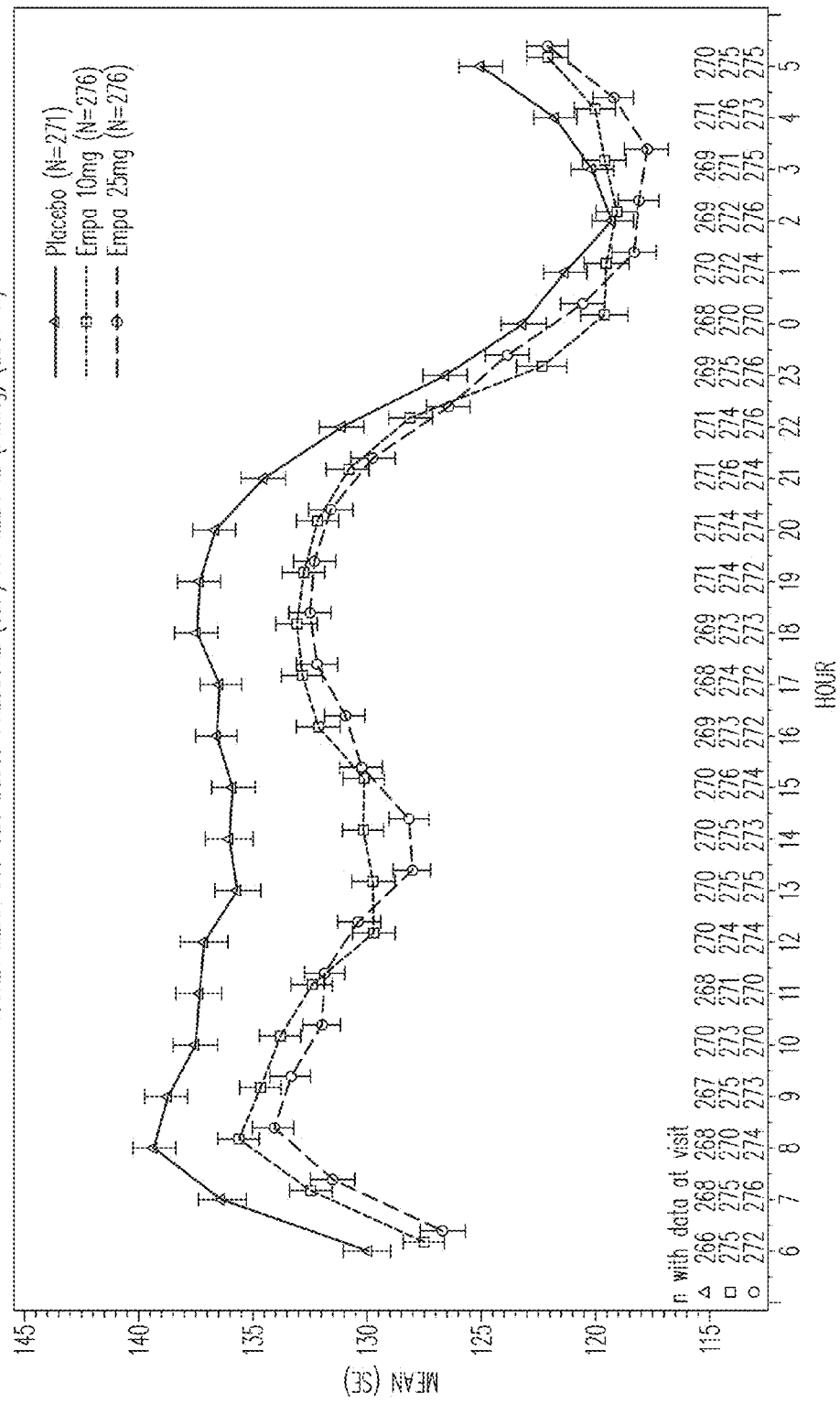
FIG. 14: Hourly mean Systolic Blood Pressure (SBP) at Week 12 (mmHg).
Figure 15:
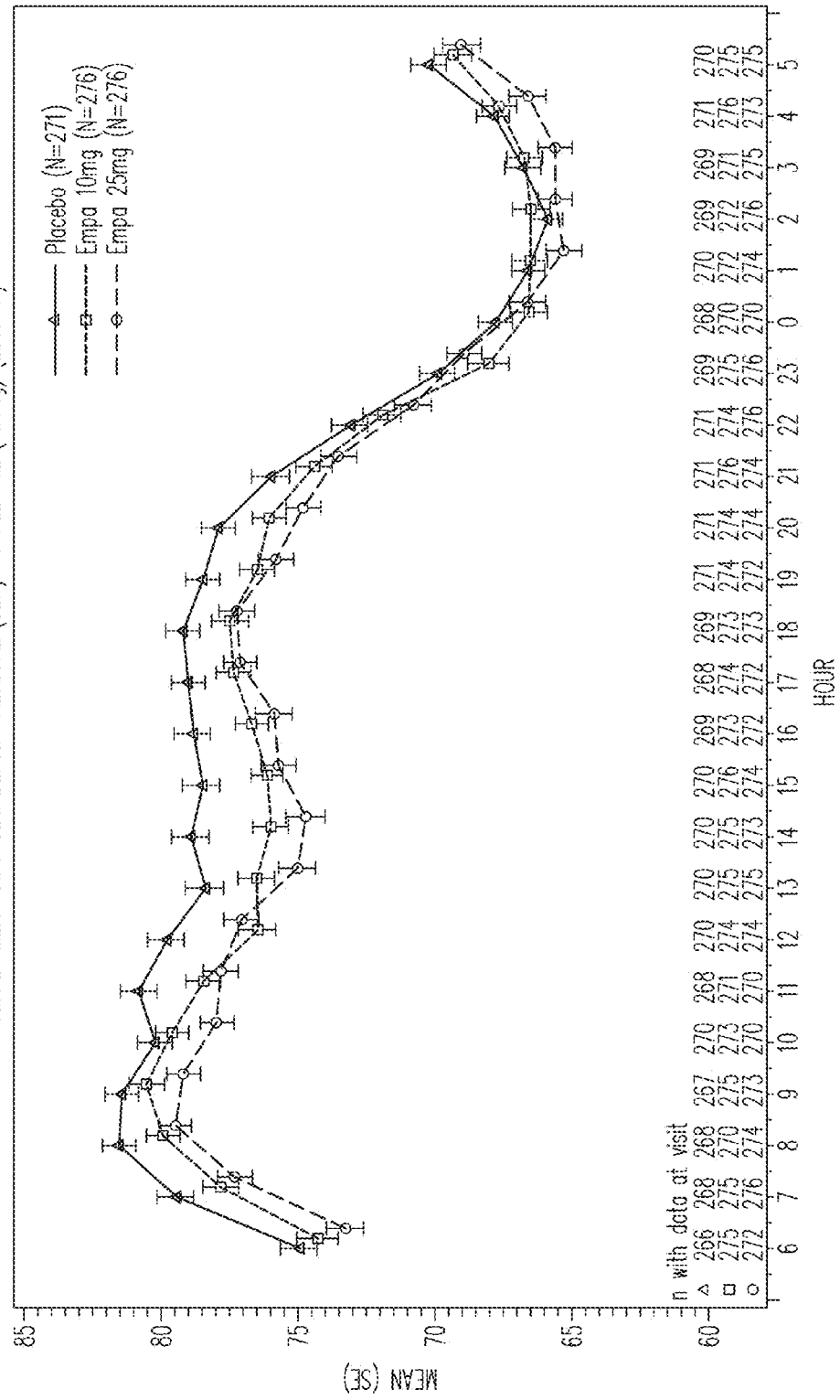
FIG. 15: Hourly mean Systolic Blood Pressure (SBP) at Week 12 (mmHg).

Empagliflozin (10 mg and 25 mg) was administered orally once daily over 12 weeks in hypertensive patients with type 2 diabetes mellitus. The change from baseline in hourly mean systolic blood pressure (SBP) and diastolic blood pressure (DBP) was measured over a 24-hour period after 12 weeks of treatment compared to the placebo group and is shown in FIGS. 14 and 15.

Example 3: Treatment of Patients with Type 2 Diabetes Mellitus with Elevated Cardiovascular Risk The longterm impact on cardiovascular morbidity and mortality and relevant efficacy parameters (e.g. HbA1c, fasting plasma glucose, treatment sustainability) of treatment with empagliflozin in a relevant population of patients with type 2 diabetes mellitus is investigated as follows:

Type 2 diabetes patient with elevated risk of cardiovascular events, e.g. as defined below, are treated over a lengthy period (e.g. for between approximately 6 and 8 years) with empagliflozin (optionally in combination with one or more other active substances, e.g. such as those described herein) and compared with patients who have been treated with a placebo on standard of care background medication.

Empagliflozin is administered orally once daily (10 mg/daily or 25 mg/daily). Patients are diagnosed with type 2 diabetes mellitus, are on diet and exercise regimen and are drug-naïve or pre-treated with any background therapy. Patients have a $HbA_{1c}$ of ≥7.0% and ≤10% for patients on background therapy or $HbA_{1c}$≥7.0% and ≤9.0% for drug-naïve patients. Patients with an elevated cardiovascular risk are defined as having at least one of the following:

Confirmed history of myocardial infarction; or
Evidence of multivessel coronary artery disease, in 2 or more major coronary arteries, irrespective of the revascularization status, i.e.
  a) Either the presence of a significant stenosis (imaging evidence of at least 50% narrowing of the luminal diameter measured during a coronary angiography or a multi-sliced computed tomography angiography), in 2 or more major coronary arteries,
  b) Or a previous revascularisation (percutaneous transluminal coronary angioplasty with or without stent, or coronary artery bypass grafting), in 2 or more major coronary arteries,
  c) Or the combination of previous revascularisation in one major coronary artery (percutaneous transluminal coronary angioplasty with or without stent, or coronary artery bypass grafting), and the presence of a significant stenosis in another major coronary artery (imaging evidence of at least 50% narrowing of the luminal diameter measured during a coronary angiography or a multi-sliced computed tomography angiography),
  Note: A disease affecting the left main coronary artery is considered as a 2-vessel disease.
Evidence of a single vessel coronary artery disease with:
  a) The presence of a significant stenosis i.e. the imaging evidence of at least 50% narrowing of the luminal diameter of one major coronary artery in patients not subsequently successfully revascularised (measured during a coronary angiography or a multi-sliced computed tomography angiography)
  b) And at least one of the following (either (i) or (ii)):
    i. A positive non invasive stress test, confirmed by either:
      1. A positive exercise tolerance test in patients without a complete left bundle branch block, Wolff-Parkinson-White syndrome, or paced ventricular rhythm, or
      2. A positive stress echocardiography showing regional systolic wall motion abnormalities, or
      3. A positive scintigraphic test showing stress-induced ischemia, i.e. the development of transient perfusion defects during myocardial perfusion imaging;
    ii. Or patient discharged from hospital with a documented diagnosis of unstable angina within 12 months prior to selection.
Episode of unstable angina with confirmed evidence of coronary multivessel or single vessel disease as defined above.
History of ischemic or haemorrhagic stroke
Presence of peripheral artery disease (symptomatic or not) documented by either: previous limb angioplasty, stenting or bypass surgery; or previous limb or foot amputation due to circulatory insufficiency; or angiographic evidence of significant (>50%) peripheral artery stenosis in at least one limb; or evidence from a non-invasive measurement of significant (>50% or as reported as hemodynamically significant) peripheral artery stenosis in at least one limb; or ankle brachial index of <0.9 in at least one limb.

Criteria for efficacy are for example change from baseline in: $HbA_{1c}$, Fasting Plasma Glucose (FPG), weight, waist circumference and blood pressure at weeks 12, 52, once a year, and end of study.

The time to first occurrence of any of the adjudicated components of the primary composite Major Adverse Cardiovascular Event (MACE) endpoint (cardiovascular death (including fatal stroke and fatal myocardial infarction), non fatal stroke, nonfatal myocardial infarction (MI) is determined in patients treated with empagliflozin compared to placebo.

The time to the first occurrence of the following adjudicated events (treated as a composite): CV death (including fatal stroke and fatal MI), non-fatal MI (excluding silent MI), non-fatal stroke and hospitalization for unstable angina pectoris is also determined in patients treated with empagliflozin compared to placebo.

Also determined are the occurrence of and time to each of the following events:
Silent MI.
Heart failure requiring hospitalization
New onset albuminuria defined as ACR≥30 mg/g
New onset macroalbuminuria≥300 mg/g.
Composite microvascular outcome defined as:
  1) Need for retinal photocoagulation
  2) Vitreous haemorrhage
  3) Diabetes-related blindness
  4) New or worsening nephropathy defined as:
    4a) New onset of macroalbuminuria; or 4b) Doubling of serum creatinine level accompanied by an eGFR (based on modification of diet in renal disease (MDRD) formula)≤45 mL/min/1.73 m$^2$; or 4c) Need for continuous renal replacement therapy; or d) death due to renal disease.

Also determined are the occurrence of and time to each of the following adjudicated events:
CV death (including fatal stroke and fatal MI)
non-fatal MI
non-fatal stroke
Hospitalization for unstable angina
All cause mortality
TIA
coronary revascularization procedures.

Example 4: Treatment of Type 2 Diabetes Mellitus

Treating patients with type 2 diabetes mellitus with empagliflozin, in addition to producing an acute improvement in the glucose metabolic situation, prevents a deterioration in the metabolic situation in the long term. This can be observed is patients are treated for a longer period, e.g. 3 months to 1 year or even 1 to 6 years, with a combination according to the invention and are compared with patients who have been treated with other antidiabetic and/or anti-obesity medicaments. There is evidence of therapeutic success compared with other treatments if no or only a slight increase in the fasting glucose and/or HbA1c value is observed. Further evidence of therapeutic success is obtained if a significantly smaller percentage of the patients treated with a combination according to the invention, compared with patients who have received another treatment, undergo a deterioration in the glucose metabolic position (e.g. an increase in the HbA1c value to >6.5% or >7%) to the point where treatment with an (additional) oral antidiabetic medicament or with insulin or with an insulin analogue is indicated.

Example 5: Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a treatment according to the invention in the treatment of insulin resistance.

Example 6: Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a combination treatment according to the invention in the treatment of hyperglycaemia.

Example 7: Effect of Empagliflozin Versus Glimepiride on Beta-Cell Function

In a Phase III study the effects of empagliflozin and the SU glimepiride as second-line therapy are compared in patients with T2DM inadequately controlled with metformin immediate release (IR) and diet/exercise.

After a 2-week placebo run-in, patients are randomized to receive empagliflozin 25 mg once daily (qd) or glimepiride 1-4 mg qd double-blind for 104 weeks, in addition to metformin IR. Patients who participate in the initial 104-weeks randomization period will be eligible for a 104-week double-blind extension.

The primary endpoint is change from baseline in $HbA_{1c}$. Secondary endpoints are change from baseline in body weight, the incidence of confirmed hypoglycemia, and changes in systolic and diastolic blood pressure. Exploratory endpoints include change from baseline in FPG, the proportion of patients achieving $HbA_{1c}$<7%, and effects on various biomarkers of beta-cell function including insulin, C-peptide, HOMA-B and proinsulin to insulin ratio, first and second phase insulin secretion after a meal tolerance test.

In addition, primary, secondary and exploratory endpoints are evaluated in a sub-group of patients with Latent Autoimmune Diabetes in Adulthood (LADA), identified by the presence at baseline of autoantibodies against insulin, islet cell cytoplasm, glutamic acid decarboxylase 65 or the intracytoplasmic domain of the tyrosine phosphatase-like protein IA-2.

Example 8: Effect of Empagliflozin Arterial Stiffness

Blood pressure, arterial stiffness, heart rate variability (HRV) and circulating adrenergic mediators were measured during clamped euglycemia and hyperglycemia in 40 normotensive patients with T1 D. Studies were repeated after 8 weeks of empagliflozin (25 mg daily).

Augmentation index (AIx) for the radial and carotid arteries as well as a derived aortic AIx and carotid, radial and femoral pulse wave velocities (PWV) are measured for assessment of arterial stiffness using a SphygmoCor® System (AtCor Medical Inc., Itasca, Ill.).

During clamped euglycemic conditions, empagliflozin reduced systolic blood pressure (111±9 to 109±9 mmHg, p=0.0187), and augmentation indices at the radial (−52±16 to −57±17%, p<0.0001), carotid (+1.3±17.0 to −5.7±17.0%, p<0.0001) and aortic positions (+0.1±13.4 to −6.2±14.3%, p<0.0001) declined. Similar effects on arterial stiffness were observed during clamped hyperglycemia; however, blood pressure effects were not significant. Carotid-radial pulse wave velocity decreased significantly under both glycemic conditions (p≤0.0001), while declines in carotid-femoral pulse wave velocity were only significant during clamped hyperglycemia (5.7±1.1 to 5.2±0.9 m/s, p=0.0017). HRV, plasma noradrenaline and adrenaline remained unchanged under both glycemic conditions.

This shows that empagliflozin reduces arterial stiffness in patients with uncomplicated T1 D.

Example of Pharmaceutical Composition and Dosage Form

The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

Tablets containing 2.5 mg, 5 mg, 10 mg, 25 mg, 50 mg of active substance

| Active substance | 2.5 mg/per tablet | 5 mg/per tablet | 10 mg/per tablet | 25 mg/per tablet | 50 mg/per tablet |
|---|---|---|---|---|---|
| Wet granulation | | | | | |
| active substance | 2.5000 | 5.000 | 10.00 | 25.00 | 50.00 |
| Lactose Monohydrate | 40.6250 | 81.250 | 162.50 | 113.00 | 226.00 |
| Microcrystalline Cellulose | 12.5000 | 25.000 | 50.00 | 40.00 | 80.00 |
| Hydroxypropyl Cellulose | 1.8750 | 3.750 | 7.50 | 6.00 | 12.00 |
| Croscarmellose Sodium | 1.2500 | 2.500 | 5.00 | 4.00 | 8.00 |
| Purified Water | q.s. | q.s. | q.s. | q.s. | q.s. |
| Dry Adds | | | | | |
| Microcrystalline Cellulose | 3.1250 | 6.250 | 12.50 | 10.00 | 20.00 |
| Colloidal silicon dioxide | 0.3125 | 0.625 | 1.25 | 1.00 | 2.00 |
| Magnesium stearate | 0.3125 | 0.625 | 1.25 | 1.00 | 2.00 |
| Total core | 62.5000 | 125.000 | 250.00 | 200.00 | 400.00 |
| Film Coating | | | | | |
| Film coating system | 2.5000 | 4.000 | 7.00 | 6.00 | 9.00 |
| Purified Water | q.s. | q.s. | q.s. | q.s. | q.s. |
| Total | 65.000 | 129.000 | 257.00 | 206.00 | 409.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method to reduce the risk of cardiovascular death in a patient with type 2 diabetes mellitus, said method comprising administering empagliflozin to the patient, wherein said patient has cardiovascular disease, wherein the risk of cardiovascular death is reduced in said patient, wherein empagliflozin is administered orally in a total daily amount of 10 mg or 25 mg.

2. The method according to claim 1, wherein empagliflozin is administered as a pharmaceutical composition comprising 10 mg or 25 mg of empagliflozin.

3. A method to reduce the risk of hospitalization for heart failure in a patient with type 2 diabetes mellitus, said method comprising administering empagliflozin to the patient, wherein said patient has cardiovascular disease, wherein the risk of hospitalization for heart failure is reduced in said patient, wherein empagliflozin is administered orally in a total daily amount of 10 mg or 25 mg.

4. The method according to claim 3, wherein empagliflozin is administered as a pharmaceutical composition comprising 10 mg or 25 mg of empagliflozin.

5. A method to reduce the risk of all-cause mortality in a patient with type 2 diabetes mellitus, said method comprising administering empagliflozin to the patient, wherein said patient has cardiovascular disease, wherein the risk of all-cause mortality is reduced in said patient, wherein empagliflozin is administered orally in a total daily amount of 10 mg or 25 mg.

6. The method according to claim 5, wherein empagliflozin is administered as a pharmaceutical composition comprising 10 mg or 25 mg of empagliflozin.

7. The method according to claim 1, wherein empagliflozin is administered orally in a total daily amount of 10 mg.

8. The method according to claim 1, wherein empagliflozin is administered orally in a total daily amount of 25 mg.

9. The method according to claim 2, wherein said pharmaceutical composition comprises 10 mg of empagliflozin.

10. The method according to claim 2, wherein said pharmaceutical composition comprises 25 mg of empagliflozin.

11. The method according to claim 3, wherein empagliflozin is administered orally in a total daily amount of 10 mg.

12. The method according to claim 3, wherein empagliflozin is administered orally in a total daily amount of 25 mg.

13. The method according to claim 4, wherein said pharmaceutical composition comprises 10 mg of empagliflozin.

14. The method according to claim 4, wherein said pharmaceutical composition comprises 25 mg of empagliflozin.

15. The method according to claim 5, wherein empagliflozin is administered orally in a total daily amount of 10 mg.

16. The method according to claim 5, wherein empagliflozin is administered orally in a total daily amount of 25 mg.

17. The method according to claim 6, wherein said pharmaceutical composition comprises 10 mg of empagliflozin.

18. The method according to claim 6, wherein said pharmaceutical composition comprises 25 mg of empagliflozin.

* * * * *